United States Patent
Ho et al.

(10) Patent No.: US 8,267,089 B2
(45) Date of Patent: *Sep. 18, 2012

(54) CUSHION INSIDE A CUSHION PATIENT INTERFACE

(75) Inventors: Peter Chi Fai Ho, Pittsburgh, PA (US); Lance Ranard Busch, Trafford, PA (US); David W. Smith, Oakmont, PA (US); Elizabeth Powell Margaria, Pittsburgh, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 99 days.

This patent is subject to a terminal disclaimer.

(21) Appl. No.: 12/767,882

(22) Filed: Apr. 27, 2010

(65) Prior Publication Data

US 2010/0199992 A1    Aug. 12, 2010

Related U.S. Application Data

(63) Continuation-in-part of application No. 12/623,597, filed on Nov. 23, 2009, now Pat. No. 8,113,202, which is a continuation of application No. 11/875,496, filed on Oct. 19, 2007, now Pat. No. 7,631,644, which is a continuation of application No. 11/401,065, filed on Apr. 10, 2006, now Pat. No. 7,287,528.

(60) Provisional application No. 60/670,806, filed on Apr. 13, 2005.

(51) Int. Cl.
*A61M 11/00* (2006.01)

(52) U.S. Cl. ............................. 128/206.21; 128/206.24

(58) Field of Classification Search .............. 128/206.12, 128/206.18, 206.21, 206.22, 206.24, 206.26, 128/206.28, 207.12
See application file for complete search history.

(56) References Cited

U.S. PATENT DOCUMENTS

| | | |
|---|---|---|
| 4,971,051 A | 11/1990 | Toffolon |
| 5,560,354 A | 10/1996 | Berthon-Jones |
| 5,647,357 A | 7/1997 | Barnett |
| 5,884,624 A | 3/1999 | Barnett |
| 5,960,494 A | 10/1999 | Gilliland |
| 6,082,360 A | 7/2000 | Rudolph |
| 6,196,223 B1 | 3/2001 | Belfer |
| 6,397,847 B1 | 6/2002 | Scarberry |
| 6,418,928 B1 | 7/2002 | Bordewick |
| 6,513,526 B2 | 2/2003 | Kwok |
| 6,581,601 B2 | 6/2003 | Ziaee |
| 6,651,663 B2 | 11/2003 | Barnett |
| 6,729,333 B2 | 5/2004 | Barnett |
| 6,796,308 B2 | 9/2004 | Gunaratnam |
| 6,823,869 B2 | 11/2004 | Raje |
| 7,044,130 B2 | 5/2006 | Jones |
| 7,237,551 B2 | 7/2007 | Ho |

(Continued)

FOREIGN PATENT DOCUMENTS

EP    1475118 A1    10/2004

*Primary Examiner* — Steven Douglas
(74) *Attorney, Agent, or Firm* — Michael W. Haas

(57) ABSTRACT

A patient interface device that includes a mask shell and a cushion assembly. The cushion assembly includes a seal cushion and a support cushion. The seal cushion contacts a first area of a patient's face to form a seal therewith. The support cushion defines a second area over a face of such a patient when the patient interface device is being worn. The second area overlaps at least a portion of the first area.

13 Claims, 23 Drawing Sheets

U.S. PATENT DOCUMENTS

| | | |
|---|---|---|
| 7,287,528 B2 | 10/2007 | Ho |
| 2002/0005198 A1 | 1/2002 | Kwok |
| 2004/0025883 A1 | 2/2004 | Eaton |
| 2004/0045551 A1 | 3/2004 | Eaton |
| 2004/0118406 A1 | 6/2004 | Lithgow |
| 2004/0216747 A1 | 11/2004 | Jones |
| 2005/0072428 A1 | 4/2005 | Ho |
| 2006/0144399 A1 | 7/2006 | Davidowski |
| 2006/0207599 A1 | 9/2006 | Busch |
| 2007/0221228 A1 | 9/2007 | Ho |

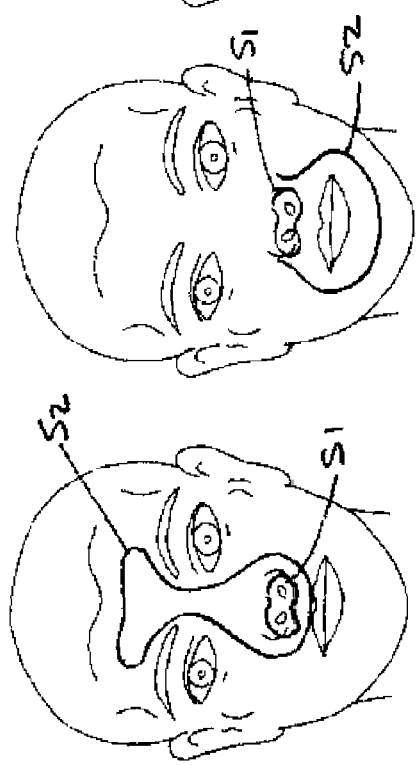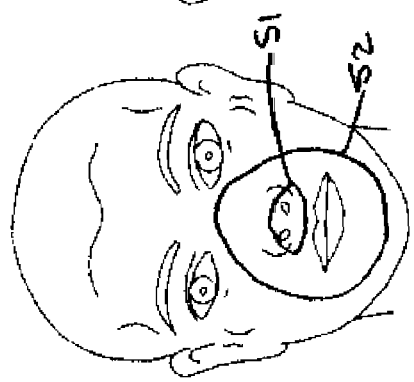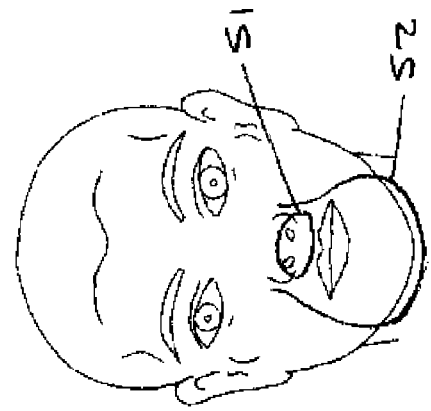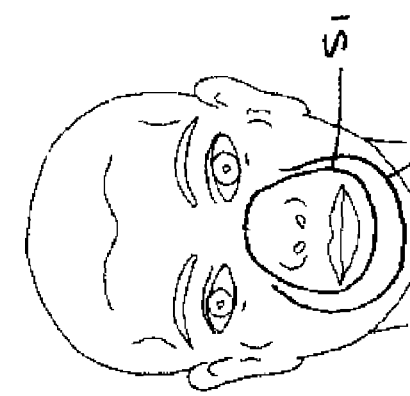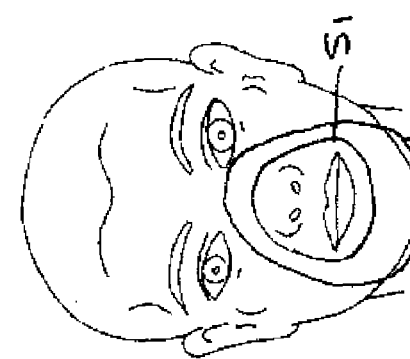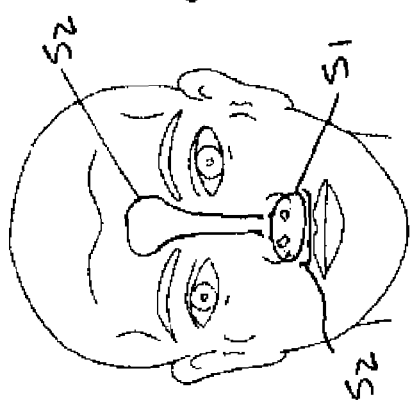

CUSHION INSIDE A CUSHION PATIENT INTERFACE

CROSS-REFERENCE TO RELATED APPLICATIONS

This application is a Continuation-in-Part under 35 U.S.C. §120 of U.S. patent application Ser. No. 12/623,597, filed Nov., 23, 2009, which is a Continuation under 35 U.S.C. §120 of U.S. patent application Ser. No. 11/875,496, filed Oct. 19, 2007, now U.S. Pat. No. 7,631,644, which is a Continuation under 35 U.S.C. §120 of U.S. patent application Ser. No. 11/401,065, filed Apr. 10, 2006, now U.S. Pat. No. 7,287,528, which claims priority under 35 U.S.C. §119(e) from provisional U.S. patent application No. 60/670,806 filed Apr. 13, 2005, the contents of which are incorporated herein by reference.

BACKGROUND OF THE INVENTION

1. Field of the Invention

The present invention generally relates to a patient interface device for use in a pressure support system that supplies a flow of gas to the airway of a patient, and, in particular to a patient interface device that includes dual-cushion support and to a pressure support system that includes such a patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Typically patient interface devices include a mask shell having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provide a tight enough seal against a patient's face without discomfort. A problem arises in that in order for the mask to maintain a seal without any undue gas leaks around the periphery of the mask, the mask may be compressed against the patient's face.

Many patient interface devices have been developed that attempt to balance the competing interests of patient comfort versus minimizing leakage. In addressing this issue, many patient interface devices have focused on the design of the cushion. Early cushion designs were typically a flap of material or a balloon, i.e., air-filled cushion, that contacted the face of the user. Further design developments include contouring the patient contacting portion of the cushion and/or making the seal customizable to the surface or underlying tissues of the user. Still further cushions have employed multiple flaps so that the outermost flap provides a sealing function. See, e.g., U.S. Pat. No. 4,791,051 to Toffolon.

Although these conventional patient interface devices have advanced the art, the need still exists for a patient interface device that improves upon existing devices, for example, to maximize patient comfort while minimizing leak, during delivery of a positive airway pressure or flow of gas to the airway of the user. For example, many conventional patient interface devices tend to focus the strapping force applied on the patient to a relative small area of the patient's face around the nose, mouth, or both. Existing patient interfaces also may not provide a stable platform that supports the cushion on the patient's face.

SUMMARY OF THE INVENTION

Accordingly, it is an object of the present invention to provide a patient interface device that overcomes the shortcomings of conventional patient interface devices. This object is achieved according to one embodiment of the present invention by providing a patient interface device that includes a mask shell, a seal cushion, and a support cushion. The seal cushion contacts a first area of a patient's face to form a seal therewith. The support cushion defines a second area over a face of such a patient when the patient interface device is being worn. The second area overlaps at least a portion of the first area.

These features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 18-58 are schematic diagrams illustrating variously exemplary alternative embodiment for the engagement of the seal and support cushions on a face of a user.

DETAILED DESCRIPTION OF THE EXEMPLARY EMBODIMENTS

Figure 1:
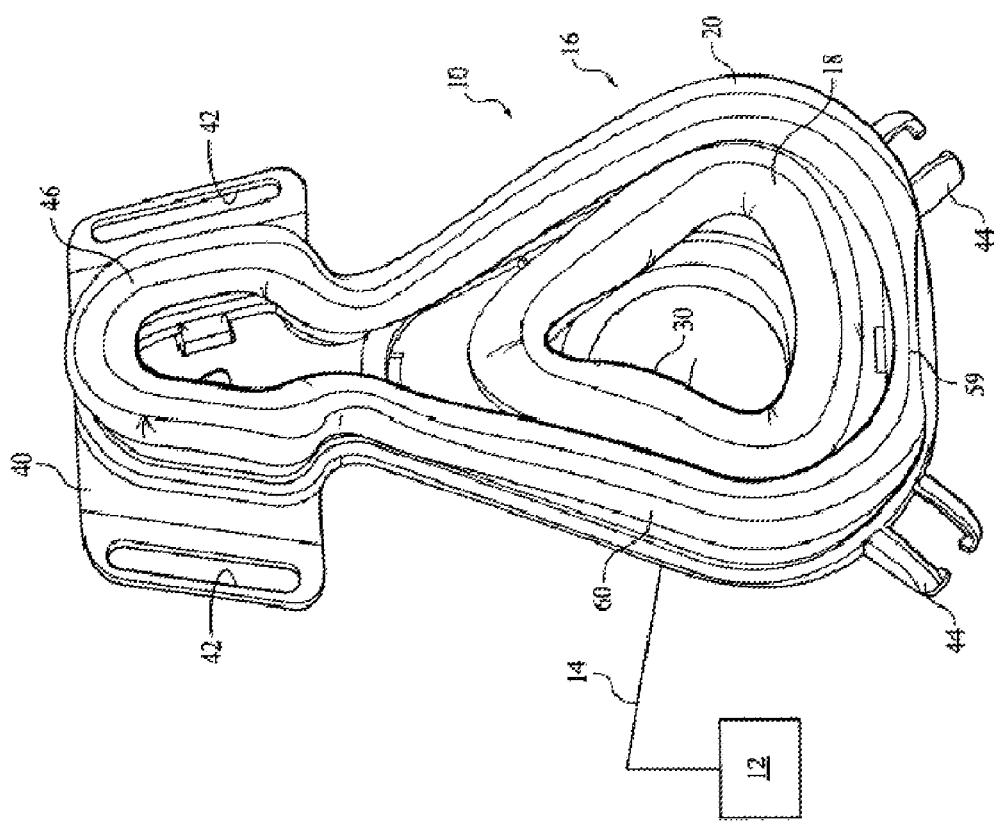
FIG. 1 is a rear perspective view of a patient interface device according to the principles of the present invention shown (schematically) connected to a gas flow/pressure generating system.
Figure 2:
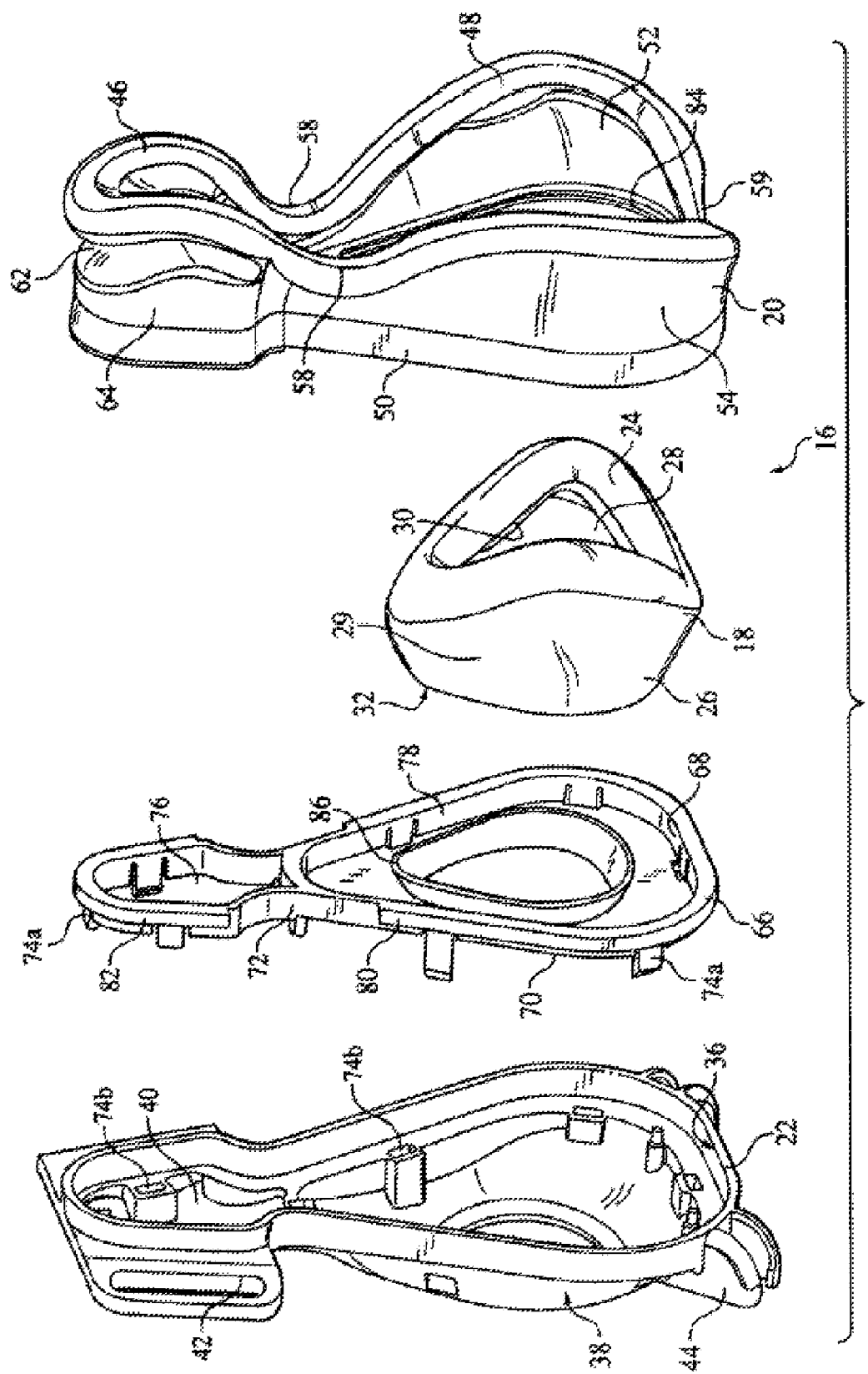
FIG. 2 is an exploded view of the patient interface device of FIG. 1.
Figure 3:
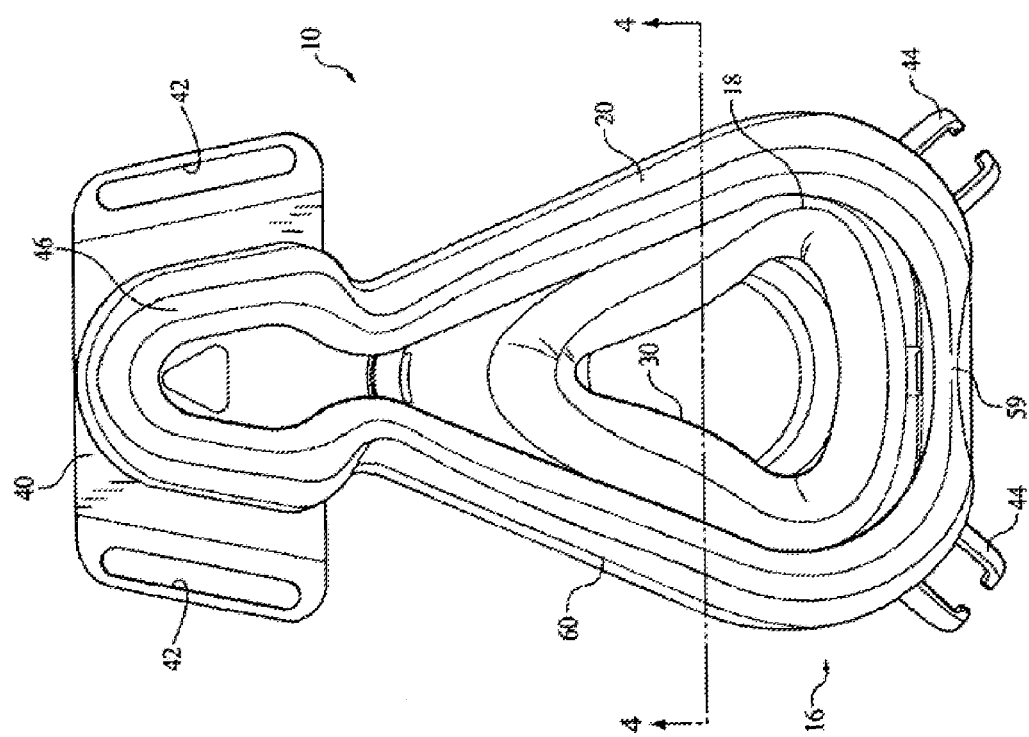
FIG. 3 is a rear view of the patient interface device of FIG. 1.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality) and the singular form of "a", "an", and "the" include plural referents unless the context clearly indicates otherwise.

FIGS. 1-4 illustrate an exemplary first embodiment of a patient interface device 10 according to the principles of the present invention. Patient interface device 10 communicates a flow of breathing gas between the patient's airway and a pressure/flow generating system 12, such as a ventilator, CPAP device, or variable pressure device, e.g., a BiPAP® device manufactured and distributed by Respironics, Inc. of Pittsburgh, Pa., or an auto-titration pressure support system.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating system 12 is also referred to as a gas flow generating device, because flow results when a pressure gradient is generated. The present invention contemplates that pressure/flow generating system 12 is any conventional system for delivering a flow of gas to an airway of a patient or for elevating a pressure of gas at an airway of the patient, including the pressure support systems summarized above and non-invasive ventilation systems.

Communicating a flow of breathing gas between the patient's airway and pressure/flow generating system 12 includes delivering a flow of breathing gas to the patient from the pressure/flow generating device and exhausting a flow of gas from the patient to ambient atmosphere. The system for delivering a breathing gas to a patient according to the present invention comprises the pressure/flow generating system that produces a flow of gas, and a conduit 14, which is also referred to as a patient circuit, having a first end portion operatively coupled to the gas flow generating device and a second end portion. Conduit 14 carries the flow of gas from pressure/flow generating device 12 during operation of the system to patient interface device 10, which is coupled to the second end portion of the conduit. Conduit 14 corresponds to any conduit suitable for communicating the flow of gas form the pressure/flow generating system to the patient interface device. A typical conduit is a flexible tube. A headgear assembly, which is not shown in the figures, attaches patient interface device 10 to the patient's head.

Patient interface device 10 includes a cushion assembly, generally indicated at 16, that includes an inner seal member or seal cushion 18 and an outer support member or support cushion 20. The patient interface device also includes a mask shell 22 and a conduit coupling member (not illustrated) that couples the mask shell to conduit 14 so that a flow of gas is communicated to the interior of the patient interface device for subsequent delivery to the patient. Conversely, gas from the patient is communicated from the patient interface device into the conduit, where an exhaust port is located.

In the illustrated exemplary embodiment, seal cushion 18 corresponds, in general, to the cushion described in U.S. Pat. Nos. 6,651,663 and 6,729,333, the contents of which are incorporated herein by reference. As perhaps best shown in FIG. 2, seal cushion 18 has a generally triangular shape and is defined from a unitary piece of soft, cushiony, elastomeric material, such as silicone, appropriately soft thermoplastic elastomers, closed cell foam, thin materials, or any combination of such materials. Seal cushion 18 has a first end portion 24 and a second end portion 26 generally opposite the first end portion. A nose receiving cavity 28 is defined in the interior of the inner seal member by side walls 29.

First end portion 24 is adapted to contact an inner perimeter area of the patient's face and includes a first opening 30 to allow passage of a least a portion of the patient's nose into nose receiving cavity 28. In the illustrated exemplary embodiment, first end portion 24 is contoured to match the general facial features of a human. Seal cushion 18 includes a base portion 32 defined in second end portion 26 and a second opening 34 defined in base portion 32. First end portion 24 of seal cushion 18 includes a first in-turned flap 35 that has a distal edge, which is generally turned into nose receiving cavity 28, and a second in-turned flap 37, which also has a distal edge that is generally turned into the nose receiving cavity. In the illustrated exemplary embodiment, flap 35 contacts the surface of the patient and deflects toward the nose receiving cavity.

Flap 35 extends around the perimeter of the first end portion and is relatively flexible to provide a leak resistant seal over the patient contacting area of the seal cushion. Flap 37 extends around a large portion of the perimeter of the first end portion, but is not present or is reduced in the area of the seal cushion that overlies the bridge of the user's nose. Flap 37 is relatively more stiff than flap 35 to provide support for the seal cushion as it is compressed. The stiffness of flap 37 and its separation from flap 35 establish the degree of support provided by flap 37. Where less support is needed, such as at the bridge of the nose (and where sealing can be difficult) the distance between flap 35 and flap 37 is increased, for example by removing flap 37 in this area. It can thus be appreciated that a variety of different configurations for flaps 35 and 37 can be employed in the cushions of the present invention.

Mask shell 22 is a generally rigid shell, and, in an exemplary embodiment of the present invention is formed from rigid plastic, such as polycarbonate. Mask shell 22 includes a patient side 36 and opposite thereto, an outer side 38. Attached to outer side 38 of mask shell 22 is a conduit coupling member (not illustrated) for coupling the patient interface device to delivery conduit 14.

In this embodiment, mask shell 22 has a generally triangular shape having a forehead support portion 40 that includes headgear attaching elements in the form of receiving holes or slots 42 disposed on either side of the upper forehead support portion for receiving headgear straps (not illustrated). In the illustrated embodiment, the lower corners of mask shell 22 also include headgear attaching elements in the form of socket attachment elements 44, which cooperate with corresponding ball elements (not illustrated) on headgear straps. The ball and socket configuration, and other headgear attachment configurations suitable for use with the present invention, are disclosed in co-pending U.S. patent application Ser. No. 10/629,366 (U.S. Pub. No. US-2004-0025883-A1), the contents of which are incorporated herein by reference. It is to be understood that the present invention contemplates using any conventional connection assembly to attach a headgear or headgear strap to mask shell 22 in this or any of the other embodiments.

The present invention contemplates that the headgear suitable for use with patient interface device 10 is any conventional headgear used in the patient interface field. For example, a typical headgear assembly comprises a headpiece that overlies a portion of the patient's crania and with headgear straps extending therefrom to adjustably connect the headgear to the mask.

In the illustrated embodiment, seal cushion 18 is a nasal cushion, meaning that it seals around the nose of the user. It is to be understood, however, that the present invention contemplates that the seal cushion can seal around any portion of the patient. For example, the seal cushion can be a nasal pillow or nasal cannula that seal against the nose, an oral/nasal seal that seals around the mouth and nose, or an oral seal that seals around the mouth.

Support cushion 20 has a generally triangular shape having an elongated upper corner. Support cushion 20 surrounds or encircles side walls 29 of seal cushion 18 and includes an integrated forehead support portion 46 at its upper extent. Support cushion 20 is preferably similar in form to a conventional mask cushion, such as a nasal or oral/nasal mask, which contacts the perimeter of a patient's facial area. Support cushion 20 is preferably formed from a unitary piece of soft, cushiony, elastomeric material, such as silicone, appropriately soft thermoplastic elastomers, or gel materials. The flexibility of the material as well as the geometry will allow support cushion 20 to conform to the patient's facial contours in a passive manner without noticeable adjustment.

Figure 4:
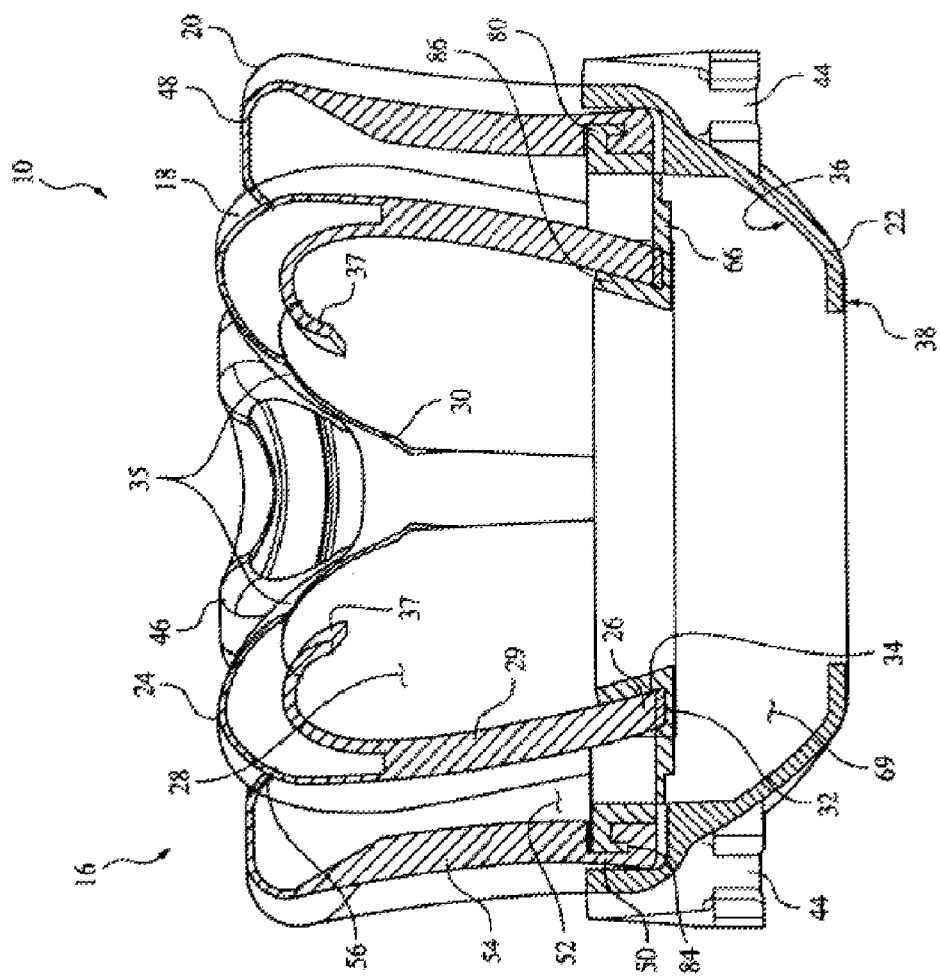
FIG. 4 is a sectional view of the patient interface device of FIG. 1 taken along line 4-4 of FIG. 3.
Figure 5:
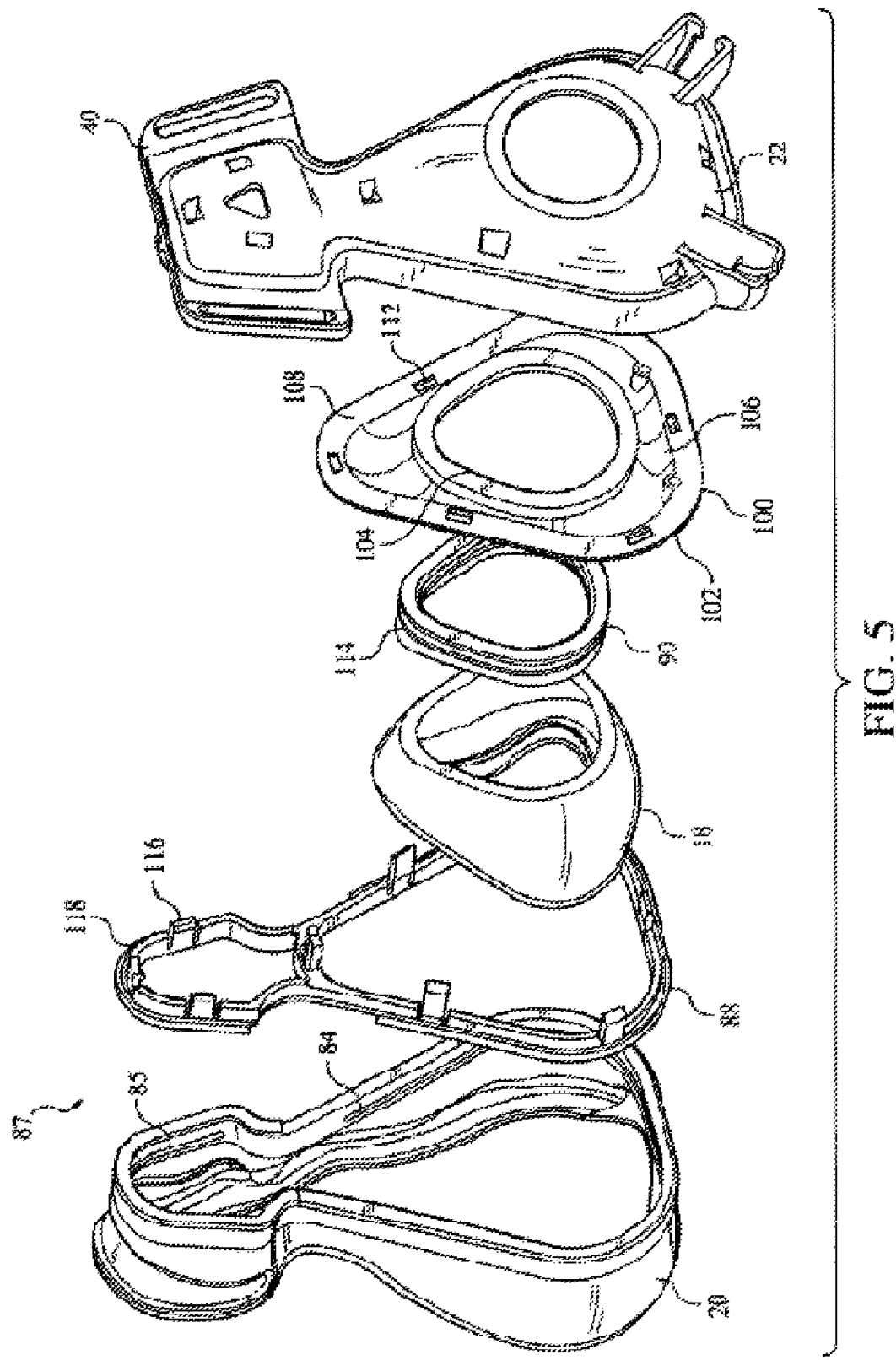
FIG. 5 is an exploded view of a patient interface device according to a second embodiment of the present invention.
Figure 6:
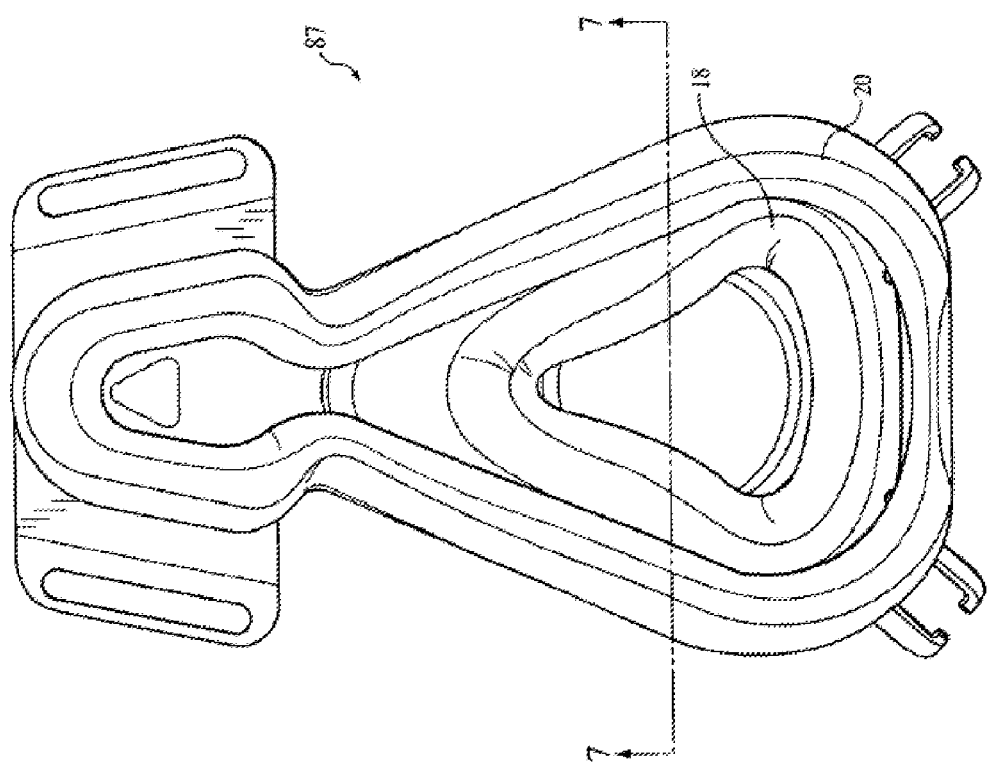
FIG. 6 is a rear view of the patient interface device of FIG. 5.
Figure 7:
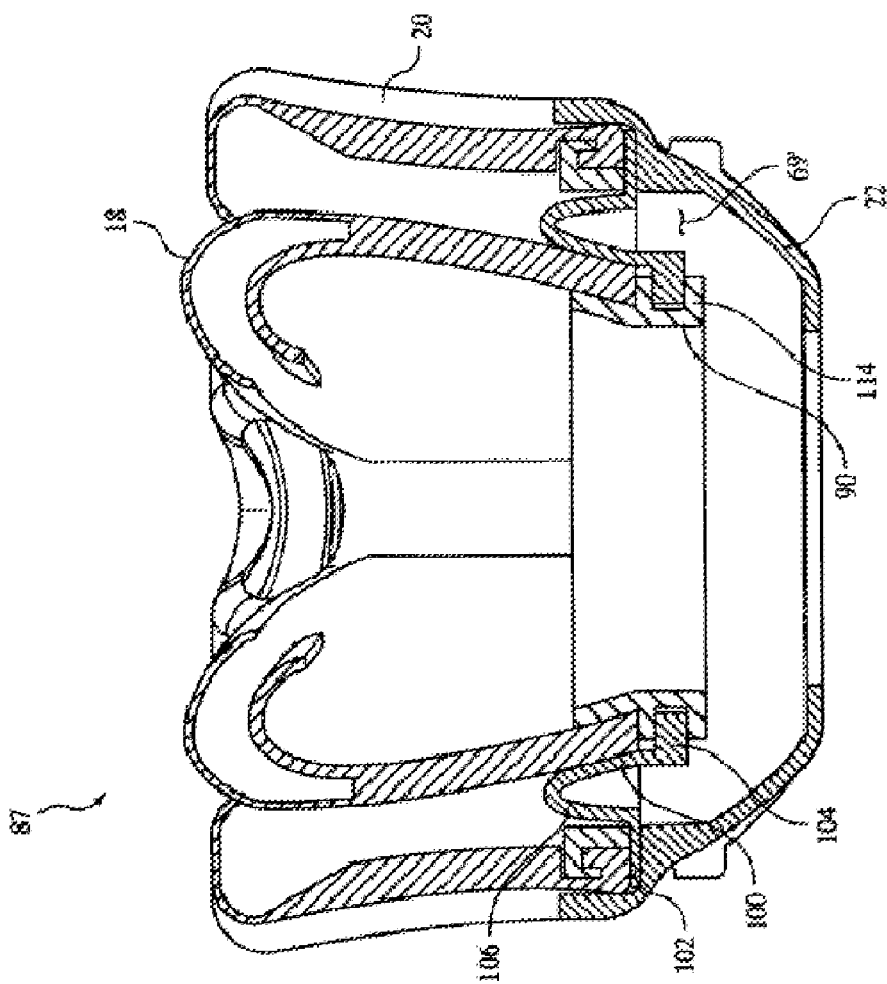
FIG. 7 is a sectional view of the patient interface device of FIG. 5 taken along line 7-7 of FIG. 6.

Seal cushion 18 is structured to have a slightly higher profile than support cushion 20, see, e.g., FIG. 4. In use, seal cushion 18 will compress slightly to form a seal with the patient's face, while support cushion 20 will provide support over a relatively larger perimeter area on the patient. This relatively large patient contacting area of the support cushion widely distributes the compressive forces acting on the patient interface device to secure the patient interface device against the surface of the user.

Integrated forehead support portion 46 of support cushion 20 eliminates the need for a separate forehead cushion, as found in many commercially available masks. Forehead support portion 46 achieves a comfortable support for the forehead passively and without active adjustment, allowing an infinite number of position adjustments. The present invention, however, contemplates that support cushion 20 is formed without a forehead support portion such that the support stands alone, supporting the nose or oral-nasal perimeter areas only.

Support cushion 20 has a first end portion 48 and a second end portion 50 generally opposite the first end portion. A seal cushion receiving cavity 52 is defined by side walls 54. First end portion 48 is adapted to generally contact an outer perimeter area of the patient's face, but is not necessarily in contact with the entire outer perimeter. That is, support cushion 20 need not serve as sealing member and does not provide a leak resistant seal for the flow of gas to the airway of the patient. Nevertheless, the present invention contemplates that the support cushion and the seal cushion can have similar configurations and be made from similar materials or combinations of materials. For example, support cushion 20 can include multiple flaps, lips, or rims at first end portion 48 and the first end portion can be contoured to match the facial features of a human, in general.

First end portion 48 also includes an in-turned flap 56, which is generally turned into seal cushion receiving cavity 52. The present invention also contemplates forming support cushion 20 from a solid formation, for example, from a gel material, or from a combination of materials. First end portion 48 also includes a dip portion 58 between forehead support portion 46 and a lower portion 60 of support cushion 20. Dip portion 58 segregates forehead portion 46 and lower portion 60 from each other to provide individual passive adjustment of the two portions. Dip portion 58 does not need to be in sealing contact with the patient's facial area. Support cushion 20 further includes a bottom portion 59 having a contoured area that also does not need to be in sealing contact with the patient's facial area. The two side areas of lower portion 60 provide most of the support.

Forehead support portion 46 further includes an integrated grooved area 62 or pleat defined in side wall 54 of forehead support portion 46 of support cushion 20. Grooved area 62 provides a floating effect to provide stability. Side wall 54 has an area 64 below grooved area 62 that is substantially thicker than the area above it to provide support. A cushion having this type of grooved area is described in co-pending U.S. provisional patent application Ser. No. 11/312,026, the contents of which are incorporated herein by reference.

In the embodiment illustrated in FIGS. 1-4, seal cushion 18 and support cushion 20 are coupled together and are coupled to mask shell 22 by a mounting member 66. Mounting member 66 has a shape corresponding generally to that of support cushion 20 and mask shell 22, and includes a patient side 68 and opposite thereto, an outer side 70 with a sidewall 72 therebetween. Outer side 70 includes multiple snap attachment features 74a, which are receivable in corresponding snap attachment features 74b on patient side 36 of mask shell 22. In the present embodiment, mounting member 66 is defined from a relatively rigid material.

Mounting member 66 includes a forehead portion 76 and a lower portion 78. The sidewall 72 of lower portion 78 includes an outwardly extending lip 80. Sidewall 72 of forehead portion 76 also includes an outwardly extending lip 82. The inner perimeter of support cushion 20 is coupled to the outer perimeter of mounting member 66, and lips 80, 82 are insertable into corresponding grooves provided on forehead portion 46 and lower portion 60 of support cushion 20. These grooves correspond to grooves 84, 85 shown in the earlier figures. The present invention contemplates using any suitable numbers of snap attachment features and other mechanical or non-mechanical means for attaching the mounting member to mask shell 22. The present invention further contemplates other mechanical or non-mechanical means for attaching support cushion 20 to mounting member 66, such as by gluing.

Mounting member 66 further includes a triangular-shaped angled wall 86 extending from its patient side. Angled wall 86 is insertable into the interior of base portion 32 of seal cushion 18 to secure the seal cushion to the mounting member. The present invention contemplates other mechanical or non-mechanical means for attaching seal cushion 18 to mounting member 66 such as by gluing.

Figure 8:
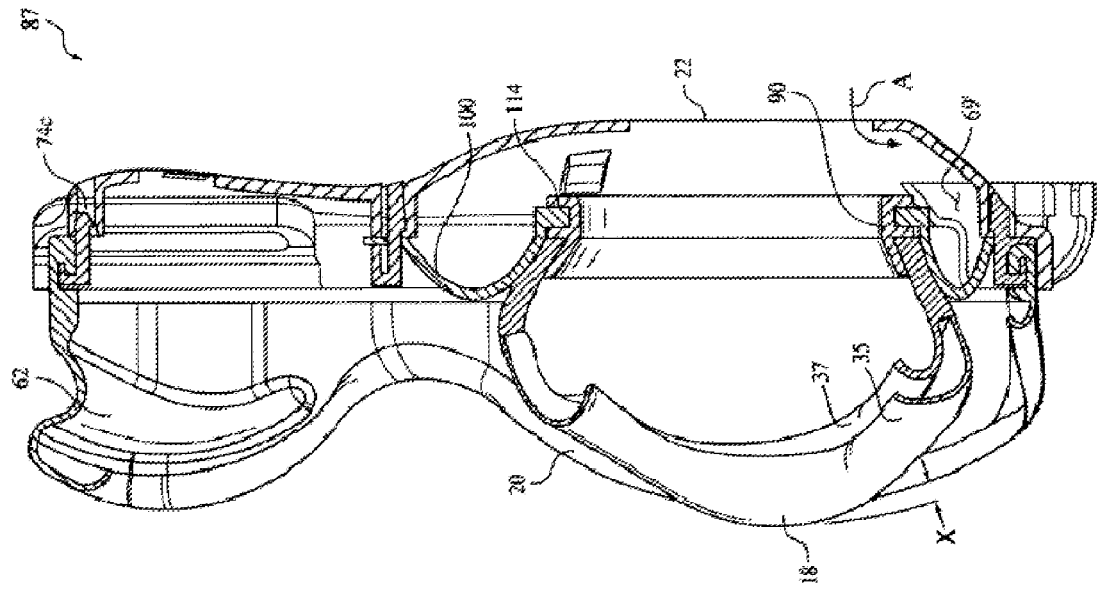
FIG. 8 is a side sectional view of the patient interface device of FIG. 5.

The arrangement between mounting member 66 and mask shell 22 provides a reservoir 69 between these two elements. This reservoir effectively functions as a water trap for any water or other fluid that may enter the mask from conduit 14. This is perhaps best illustrated in FIG. 8. Water or other fluid may condense on the walls of conduit 14, especially when a humidifier is used in the pressure/flow generating system. This fluid may flow toward the mask as indicated by arrow A and collect in reservoir 69. Thus, reservoir 69 effectively functions as a water trap to prevent or minimize the change of fluid contacting the user. A mask having such features is disclosed in copending U.S. provisional patent application Ser. No. 11/300,052, the contents of which are incorporated herein by reference.

An alternative exemplary embodiment of a patient interface device 87 according to the principles of the present invention is illustrated in FIGS. 5-8. In this embodiment, many features are similar to those illustrated in FIGS. 1-4. Thus, the description of this embodiment will focus primarily on the features of the patient interface device unique to each embodiment. This alternative embodiment is provided primarily to show a different possible configuration for coupling the cushions to the mask shell. It is to be understood, however, that the present invention contemplates other configurations for the patient interface components and mixing and matching of the features of the patient interface devices illustrated in all of these embodiments.

Like in the embodiment of FIGS. 1-4, patient interface device 87 includes a seal cushion 18, support cushion 20, and a mask shell 22. In this exemplary embodiment, seal cushion 18 and support cushion 20 are coupled together and to mask shell 22 by a rigid holding member 88, a retaining ring 90, and a flexible connecting member or rolling diaphragm 100. Rolling diaphragm 100 corresponds to the rolling diaphragm disclosed in co-pending U.S. provisional patent application Ser. No. 11/374,580 (the '580 application), the contents of which is incorporated by reference herein.

Rolling diaphragm 100 according to the present invention is operatively connected between seal cushion 18 and mask shell 22. In the illustrated embodiment, rolling diaphragm 100 is generally triangular in shape and includes a substantially concentric outer rim 102 and inner rim 104. A rolling element in the form of a flexible wall or membrane 106 extends between the outer and inner rims. Rolling diaphragm 100 is preferably molded of a high modulus thermoplastic elastomer or rubbery material to provide the desired flexibility. The material may be the same or different material than the one used for the seal cushion 18 or support cushion 20. In the illustrated embodiment, flexible wall or membrane 106 has a generally uniform thickness and a substantially U-shaped cross-section when not under pressure, e.g., when a flow of gas is not being delivered to the patient interface device. Rolling diaphragm 100 changes its shape depending on the force imparted to it through seal cushion 18 or mask shell 22 so that the position of the seal cushion relative to the mask shell can change. The U-shaped flexible membrane 106 is pointed away from mask shell 22.

Rolling diaphragm 100 isolates the forces and acts as a buffer between seal cushion 18 and mask shell 22. Rolling diaphragm 100 also acts as a flexible joint allowing relative angular and displacement movement between seal cushion 18 and mask shell 22. This allows the seal cushion to self-align on the surface of the patient when the patient interface device is donned by the user. Rolling diaphragm 100 also isolates seal cushion 18 from movement of the patient's head or support cushion 20 and displacement of the conduit tubing or headgear.

Outer rim 102 of rolling diaphragm 100 includes an annular flange 108 extending substantially perpendicularly from flexible wall membrane 106 of rolling diaphragm 100. Rolling diaphragm 100 of this illustrated embodiment further includes a plurality of rectangular holes or slots 112 spaced on annular flange 108. Seal cushion 18 is attached to rolling diaphragm 100 by retaining ring 90, which also has an outer annular groove 114 for receiving inner rim 104 of rolling diaphragm 100. Holding member 88 includes a plurality of snap attachment features 116, some of which are insertable through rectangular holes 112 and then receivable in corresponding snap attachment features 74c on patient side 36 of mask shell 22. Other snap attachment features 116 on a forehead portion 118 of holding member 88 are receivable directly in the corresponding snap attachment features on forehead support portion 40 of mask shell 22.

The present invention contemplates alternative techniques for coupling the rolling diaphragm to the mask shell, many of which are described in the '580 application. The present invention further contemplates that rolling diaphragm 100 can have alternative shapes, can be formed from different materials or combinations of materials, and/or can have variations in dimensions over the overall diaphragm. Many such alternatives are disclosed in the '580 application.

Figure 9:
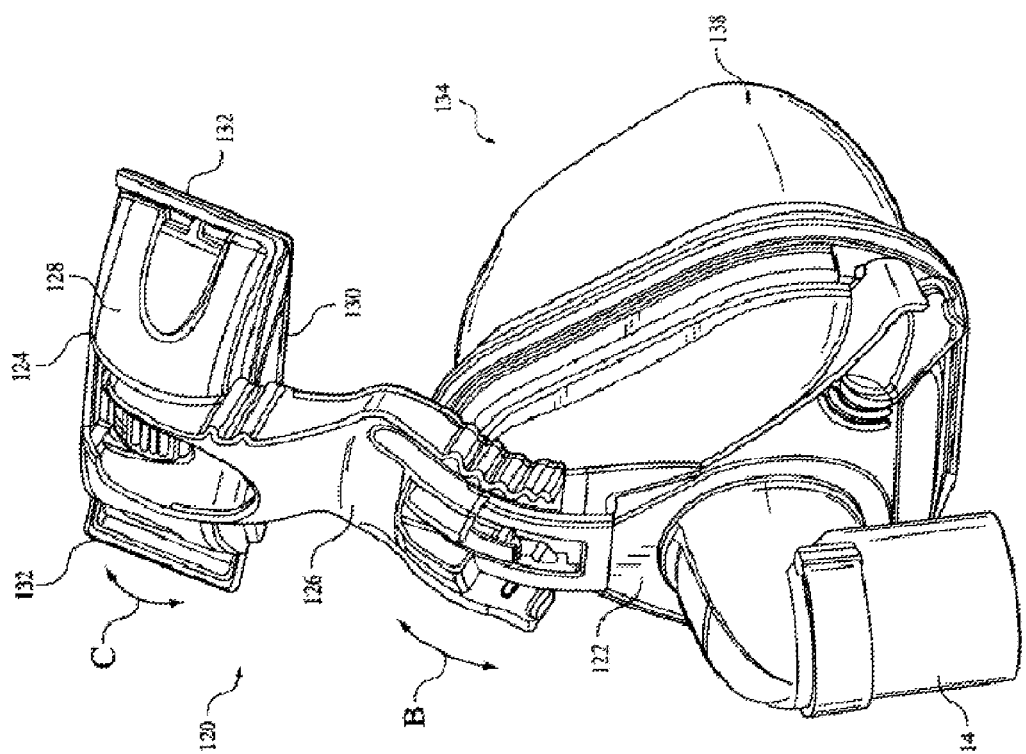
FIGS. 9 and 10 are front and rear perspective views, respectively, of a patient interface device according to a third embodiment of the present invention.
Figure 10:
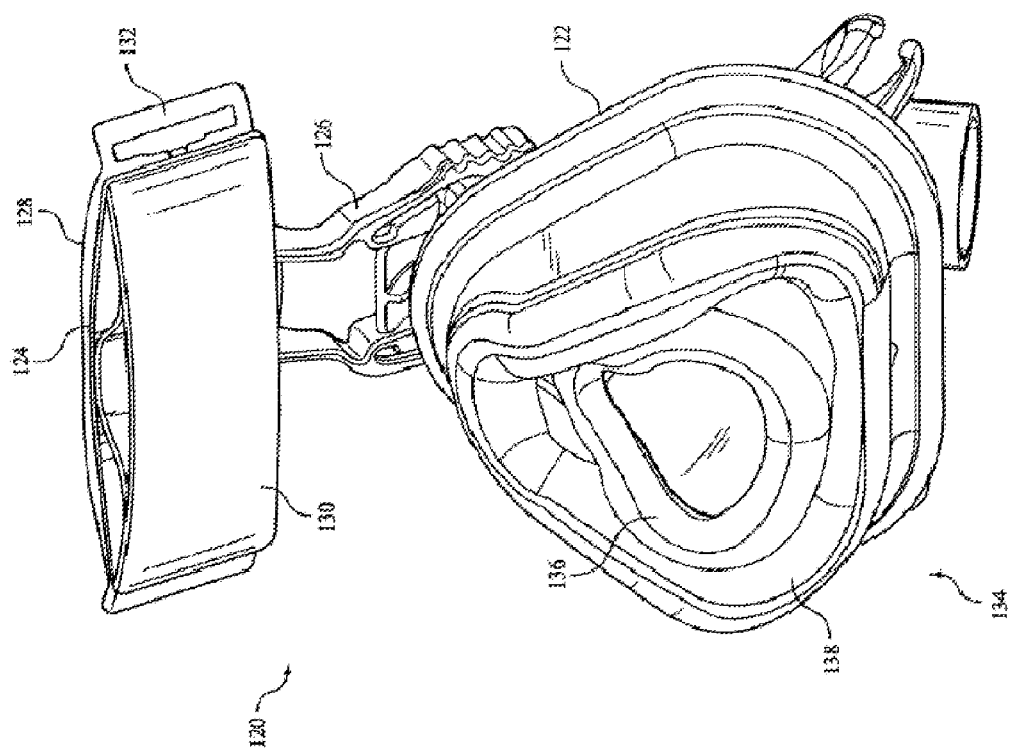

FIGS. 9 and 10 illustrate a third exemplary embodiment of a patient interface device 120 according to the principles of the present invention. In this embodiment, many features are similar to those illustrated in FIGS. 1-8. Thus, the description of this embodiment will focus primarily on the features of the patient interface device unique to each embodiment. This alternative embodiment is provided primarily to show a different possible configuration for the mask shell. This embodiment also shows that the cushion inside a cushion arrangement can be provided without the forehead portion. That is the cushion inside a cushion technique can be limited to a seal used to seal the supply of gas to the user's airway, and need not extend to the forehead as shown in previous embodiments. Again, it should be noted that the present invention contemplates other configurations for the patient interface components and mixing and matching of the features of the patient interface devices illustrated in all of these embodiments.

Patient interface device 120 includes a mask shell 122 having a forehead support assembly 124. In the illustrated embodiment, forehead support 124 includes a support arm 126, a forehead support bracket 128 coupled to the support arm, and a forehead pad 130 coupled to the support bracket. In the illustrated exemplary embodiment, support arm 126 is adjustably coupled to mask shell 122 such that the arm is movable along an arcuate path with respect to the mask shell, as indicated by arrow B. This allows the position of the forehead support bracket to be adjusted by the user for optimum comfort. Forehead support bracket 128 is also movable relative to the support arm as indicated by arrow C. This allows the forehead pad to automatically move the optimum patient contacting position when the patient interface device is donned by the user. Headgear attachments 132 are provided on each side of the forehead support bracket.

A patient interface device having many similar, if not identical features (other than the cushion inside a cushion concept of the present invention), is described in U.S. patent application Ser. No. 10/654,379 (U.S. Pub. No. US-2004-0045551-A1) the contents of which are incorporated herein by reference. It can further be appreciated that the forehead support and the components thereof, can be any one of a variety of different shapes, sizes, and configurations so long as the forehead support function is achieved. For example, the forehead pad can have other shapes, materials, combination of materials, sizes, and configurations. Similarly, the mask shell can have any one of a variety of different, shapes, sizes, and configurations, and can include additional features, such as headgear attachment portions, one or more exhaust assemblies, patient circuit connectors, or any combination thereof. Moreover, the present invention also contemplates a rigid coupling between support arm 126 and mask shell 122, between support arm 126 and support bracket 128, or both.

The present invention also contemplates eliminating the forehead support entirely, so that the patient interface device is supported on the patient by a cushion assembly 134, which is attached to the mask shell. If the forehead support is eliminated, a headgear attachment can be provided at the upper apex of the mask shell. The present invention also contemplates providing a post or other protrusion at the upper portion of the shell, i.e., the portion overlying the bridge of the nose, to which the headgear can be attached.

The present invention further contemplates providing a chin support assembly (not shown) that extends from the mask shell and contacts the user's chin or mandible. The chin support assembly can be have the same or a similar configuration to the forehead support, but extending from the lower portion of the mask to contact the user below the lips, i.e., on the chin or mandible. U.S. patent application Ser. No. 10/953,642 (U.S. Pub. No. US-2005-0072428-A1), the contents of which are incorporated herein by reference, describes examples of such chin support assemblies suitable for use in the present invention. The chin support assembly can be used alone or in combination with the forehead support assembly.

A cushion assembly 134 is coupled to mask shell 122. Cushion assembly 134 corresponds to any of the cushion assemblies described above, and includes an inner seal member or seal cushion 136 and an outer support member or support cushion 138. The seal cushion and support cushion can be coupled together using any of the techniques described herein, including a relatively rigid attachment (see FIGS. 1-4) or a flexible attachment (see FIGS. 5-8).

Figure 11:
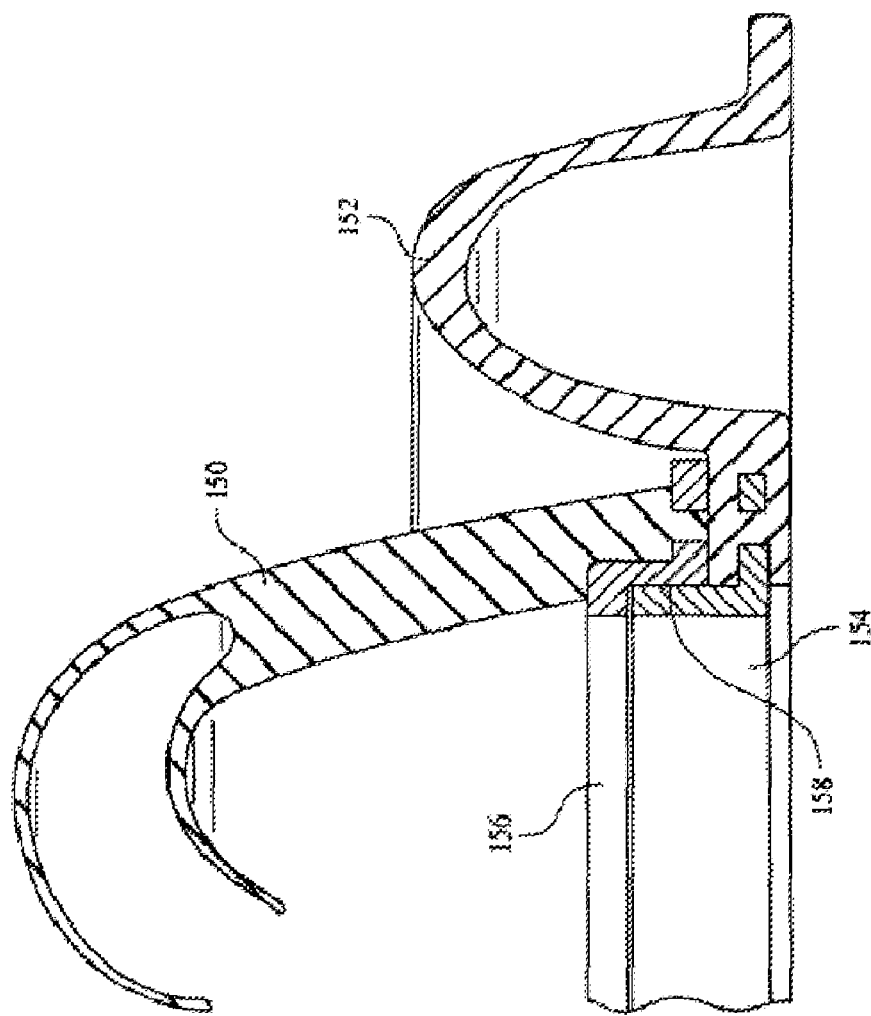
FIG. 11 is a detailed sectional view showing an exemplary technique for attaching a seal member to a flexible connecting member.

FIG. 11 is a detailed sectional view showing another technique for attaching a seal member 150 to a flexible connecting member 152. In this embodiment, the seal member is molded or otherwise bonded to a seal ring 156, and the flexible connecting member is molded or otherwise bonded to a connecting member ring 154. In an exemplary embodiment, the present invention contemplates overmolding seal 150 on ring 156 and overmolding flexible connecting member 152 on connecting member ring 154. Seal ring 156 and connecting member ring 154 are sized, configured, and arranged such that a wall of the seal ring abuts or is close to a wall of the connecting member ring at a junction indicated by reference numeral 158. These walls are joined together using any conventional technique, such as sonic welding. Of course, friction alone can be used to maintain the rings in an assembled relation. It is to be understood that other configurations for the rings and ring/seal or ring/flexible member coupling are contemplated by the present invention.

Figure 12:
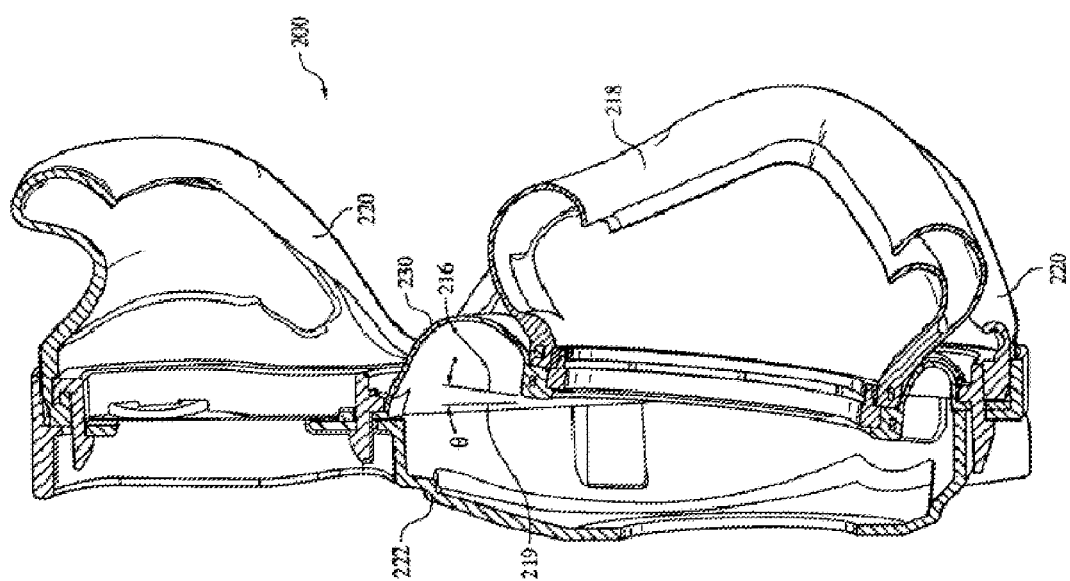
FIG. 12 is a side sectional view of a patient interface device according to a fourth embodiment of the present invention.
Figure 13:
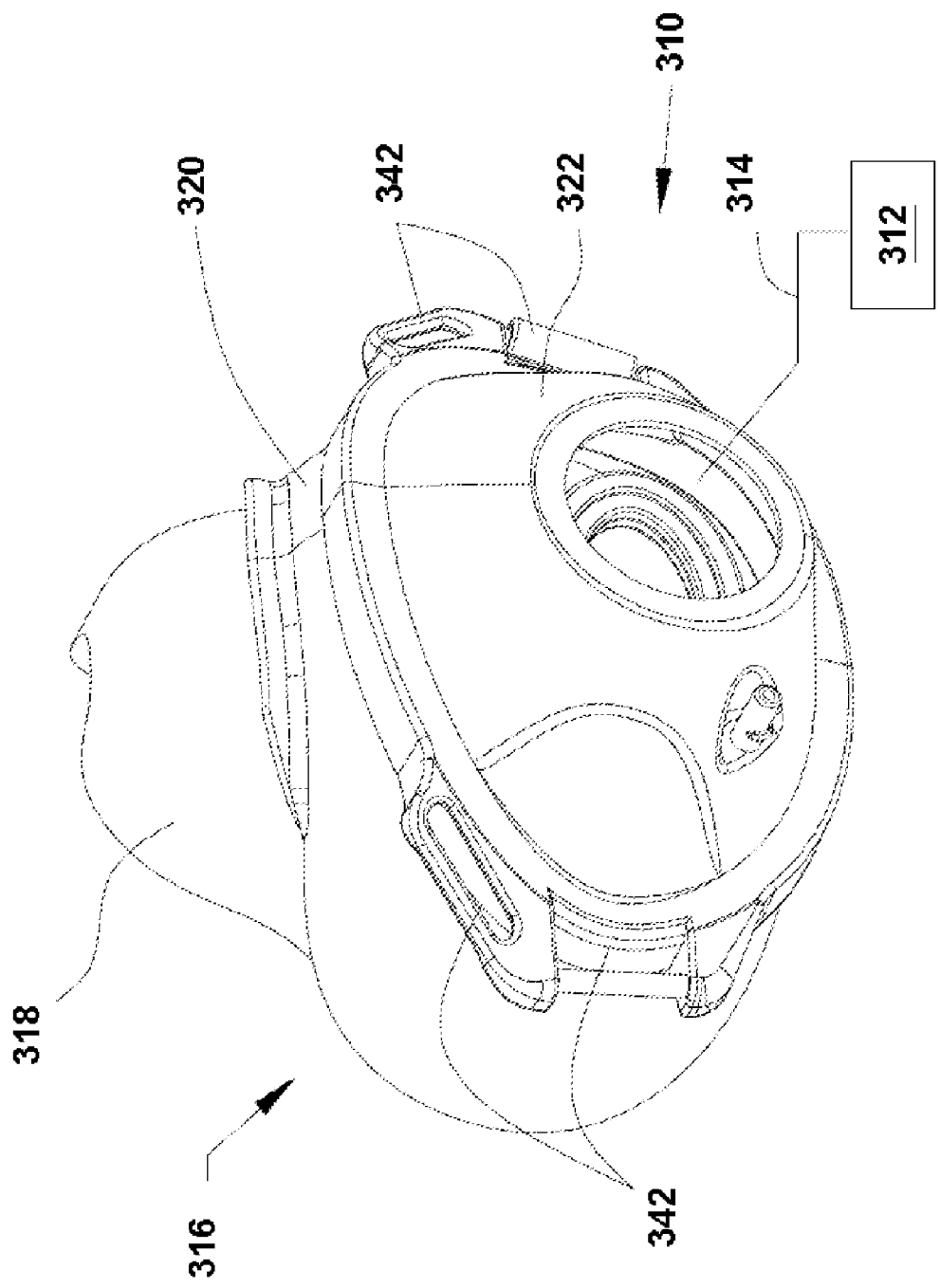
FIG. 13 is a front perspective view of a patient interface device according to a third embodiment of the present invention shown (schematically) connected to a gas flow/pressure generating system.

A fourth embodiment of a patient interface device 200 according to the principles of the present invention is illustrated in FIG. 12. Patient interface device 200 is generally similar to that shown in FIG. 8 except for the at rest positioning of seal cushion 218 relative to support cushion 220. In this exemplary embodiment, seal cushion 218 is defined in a plane 216 that is disposed at an angle θ with respect to a plane 219 defined by another portion of the patient interface device, such as shell 222 or support cushion 220. This is done to preposition seal cushion 218 so that the angle of attack on the face of the user is optimized. In an exemplary embodiment of the present invention, angle θ ranges from zero to fifteen degrees (0-15°). In this embodiment, the angle is provided by configuring a rolling diaphragm 230 in such a way that causes the tilt. Of course, other techniques for controlling the position of and/or pre-positioning the seal cushion relative to the support cushion, the shell, or other portion of the patient interface device are contemplated by the present invention.

In the illustrated embodiments, the seal cushion and support cushion are configured/arranged such that an outer (distal) edge of the seal cushion extends beyond the outer (distal) edge of the support cushion. This protrusion of the seal cushion out from the rim of the support cushion is illustrated by distance x in FIG. 8. It should be understood, however, that the present invention also contemplates configuring/arranging the seal cushion and support cushion such that the seal cushion does not extend beyond the outer edge of the support cushion in the at rest (non-deflected) position.

FIGS. 13-17 illustrate a further exemplary embodiment of a patient interface device 310 according to a third embodiment of the present invention. As in the previous embodiments, patient interface device 310 communicates a flow of breathing gas between the patient's airway and a pressure/flow generating system 312, such as a ventilator, CPAP device, or variable pressure device, e.g., a BiPAP.

Patient interface device 310 includes a cushion assembly, generally indicated at 316, that includes an inner seal member or seal cushion 318 and an outer support member or support cushion 320. Patient interface device 310 also includes a mask shell 322 and a conduit coupling member (not illustrated) that couples the mask shell 322 to conduit 314 so that a flow of gas is communicated to the interior of the patient interface device for subsequent delivery to the patient. Conversely, gas from the patient is communicated from the patient interface device into the conduit, where an exhaust port (not shown) is located.

In the illustrated exemplary embodiment, seal cushion 318 corresponds, at least in general, to the seal cushions discussed above. In an exemplary embodiment, seal cushion 318 has a generally triangular shape and is defined from a unitary piece of soft, cushiony, elastomeric material, such as silicone, appropriately soft thermoplastic elastomers, closed cell foam, gel, thin materials, or any combination of such materials.

Seal cushion 318 has a first end portion 324 and a second end portion 326 generally opposite first end portion 324. A breathing cavity 328 is defined in the interior of the seal cushion by side walls 329. First end portion 324 is adapted to contact an inner perimeter area of the patient's face and includes a first opening 330 to allow passage of at least a portion of the patient's face into breathing cavity 328. In the illustrated exemplary embodiment, first end portion 324 is contoured to match, at least generally, the human facial features about the mouth and nose. Seal cushion 318 includes a base portion 332 defined in second end portion 326 and a second opening 334 defined in base portion 332.

First end portion 324 of seal cushion 318 includes a first in-turned flap 335 that has a distal edge, which is generally turned into breathing cavity 328, and a second in-turned flap 337, which also has a distal edge that is generally turned into breathing cavity 328. In the illustrated exemplary embodiment, flap 335 contacts the surface of the patient and deflects toward breathing cavity 328.

Flap 335 extends around the perimeter of first end portion 324 and is relatively flexible to provide a leak resistant seal over the area of seal cushion 318 that contacts the patient. Flap 337 extends around a large portion of the perimeter of the first end portion, but is generally reduced in the area of the seal cushion that overlies the bridge of the user's nose. Flap 337 is relatively more stiff than flap 335 to provide support for seal cushion 318 as it is compressed. The stiffness of flap 337 and its separation from flap 335 generally establish the degree of support provided by flap 337. Where less support is needed, such as at the bridge of the nose (and where sealing can be difficult) the distance between flap 335 and flap 337 may be increased, for example by removing flap 337 in this area. It can thus be appreciated that a variety of different configurations for flaps 335 and 337 can be employed in the cushions of the present invention.

Mask shell 322 is a generally rigid shell, and, in an exemplary embodiment of the present invention is formed from rigid plastic, such as polycarbonate. Mask shell 322 includes a patient side 336, an opposite outer side 338, and an opening 340 passing therethrough. Attached to outer side 338 and opening 340 of mask shell 322 is a conduit coupling member (not illustrated) for coupling the patient interface device to delivery conduit 314. It can be appreciated that mask shell 322 can have a variety of configurations, geometries, sizes and shapes.

In the embodiment illustrated, mask shell 322 has a generally oval shape and includes headgear attaching elements in the form of receiving holes or slots 342 disposed on either side of the mask shell for receiving headgear straps (not illustrated). It is to be understood that the present invention contemplates using any conventional connection assembly to attach a headgear or headgear strap to mask shell 322 in this or any of the other embodiments.

The present invention contemplates that the headgear suitable for use with patient interface device 310 is any conventional headgear used in the patient interface field. For example, a typical headgear assembly comprises a headpiece that overlies a portion of the patient's crania and with headgear straps extending therefrom to adjustably connect the headgear to the mask.

In the illustrated embodiment, seal cushion 318 is an oral/nasal cushion, meaning that it seals around both the nose and mouth of the user. It is to be understood, however, that the present invention contemplates that the seal cushion can seal around any portion of the patient. For example, the seal cushion can be a nasal pillow or nasal cannula that seal against the nose, an oral/nasal seal that seals around the mouth and nose, or an oral seal that seals around the mouth.

Support cushion 320 has a generally oval shape having a slightly elongated or upturned upper portion. Support cushion 320 generally surrounds or encircles side walls 329 of seal cushion 318. In an exemplary embodiment, support cushion 320 is similar in form to a conventional mask cushion, such as a nasal or oral/nasal mask, which contacts the perimeter of a patient's facial area. Support cushion 320 is preferably formed from a unitary piece of soft, cushiony, elastomeric material, such as silicone, appropriately soft thermoplastic elastomers, or gel materials. The flexibility of the material as well as the geometry will allow support cushion 320 to conform to the patient's facial contours in a passive manner without noticeable adjustment.

Figure 14:
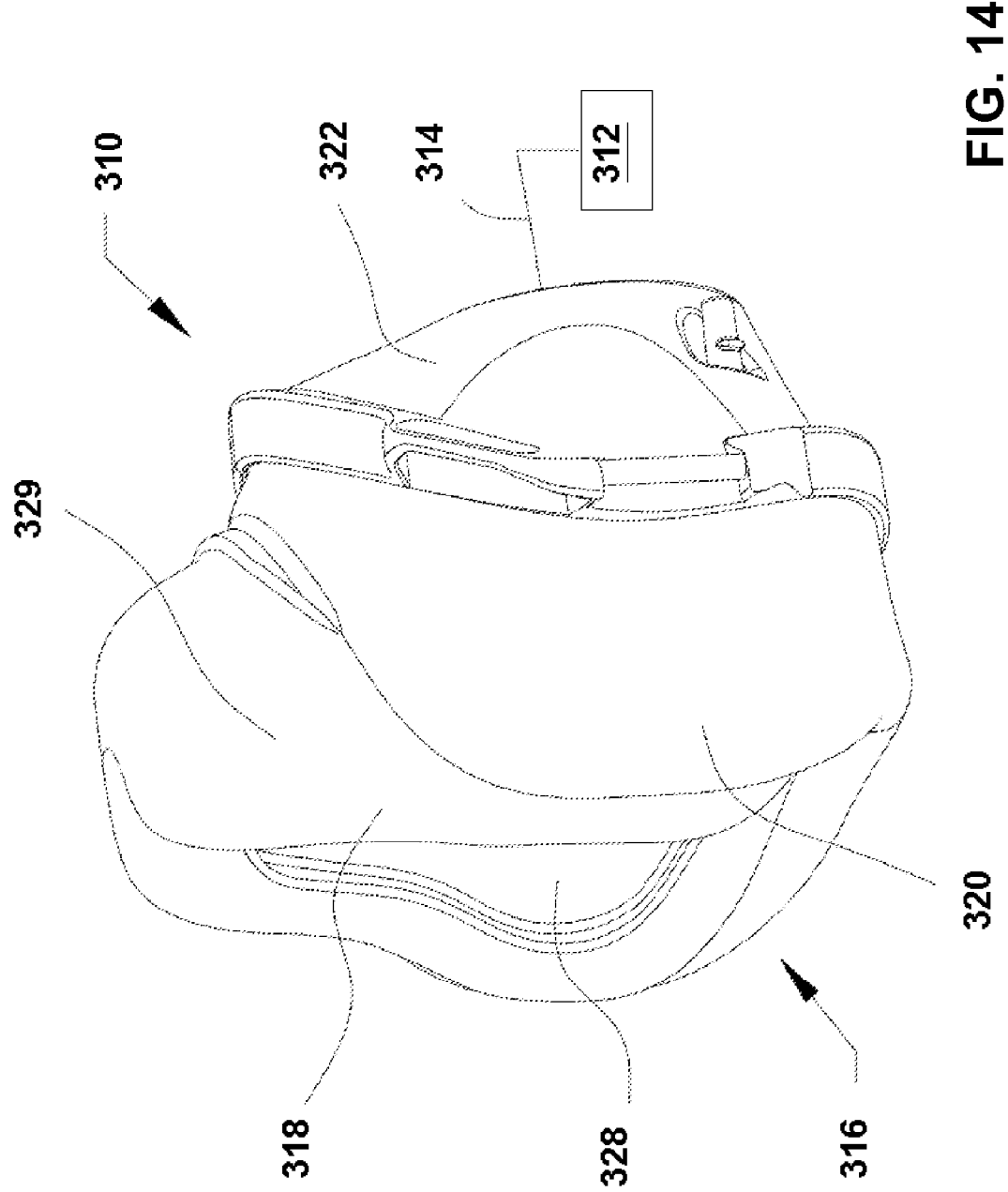
FIG. 14 is rear perspective view of the patient interface device of FIG. 13.
Figure 15:
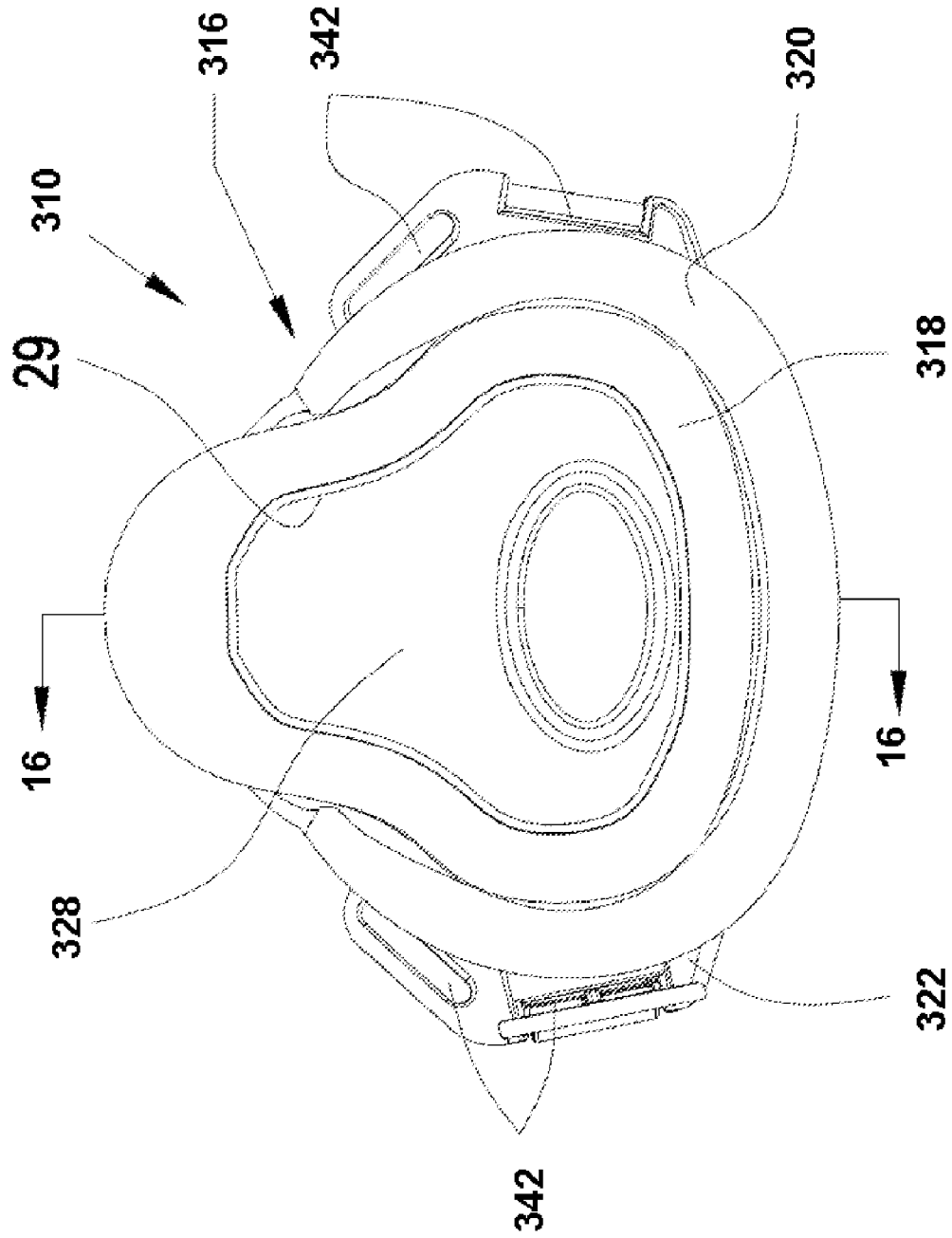
FIG. 15 is a rear view of the patient side of the patient interface device of FIGS. 13 and 12.

Seal cushion 318 is structured to have a slightly higher profile than support cushion 320, see, e.g., FIG. 14. In use, seal cushion 318 will compress slightly to form a seal with the patient's face, while support cushion 320 will provide support over a relatively larger perimeter area on the patient. This relatively large patient contacting area of the support cushion widely distributes the compressive forces acting on the patient interface device to secure the patient interface device against the surface of the user.

It can be appreciated that the seal cushion defines a first area over a face of a patient when the patient interface device is being worn by the patient. This first area necessarily encompasses at least one airway of the patient (e.g., mouth, one nare, both nares, or any combination thereof). The support cushion defines a second area over a face of a patient when the patient interface device is worn by the patient. This second area is defined by the outline of the support cushion so that even through the support cushion is not in continuous contact with the user over its entire perimeter, the support cushion nevertheless defines a second area over the user. This second area overlaps at least a portion of the first area responsive to the patient interface device being worn by a patient.

Support cushion 320 has a first end portion 348 and a second end portion 350 generally opposite first end portion 348. A seal cushion receiving cavity 352 is defined by side walls 354. First end portion 348 is adapted to generally contact an outer perimeter area of the patient's face, but is not necessarily in contact with the entire outer perimeter. That is, support cushion 320 need not serve as sealing member and does not provide a leak resistant seal for the flow of gas to the airway of the patient. Nevertheless, the present invention contemplates that the support cushion and the seal cushion can have similar configurations and be made from similar materials or combinations of materials. For example, support cushion 320 can include multiple flaps, lips, or rims at first end portion 348 and the first end portion can be contoured to match the facial features of a human, in general.

First end portion 348 also includes an in-turned flap 356, which is generally turned into seal cushion receiving cavity 352. The present invention also contemplates forming support cushion 320 from a solid formation, for example, from a gel material, or from a combination of materials. As previously mentioned, first end portion 348 further includes a slightly elongated or upturned portion, such as reinforced T-flap portion 358 along the top of support cushion 320. T-flap portion 358 is of generally more rigid construction than the adjacent turned in flap 356. In an exemplary embodiment, T-flap portion 358 is integral with and formed from the same material as the remainder of the support cushion. The present invention also contemplates that T-flap portion 358 may it be formed from a different material and bonded to the support cushion.

T-flap portion 358 is not in sealing contact with the patient's facial area. Instead, T-flap portion 358 provides support to the portion of sealing cushion 318 at or about the nasal area of the patient. T-flap portion 358 effectively serves as a replacement for the conventional forehead support arm that is typically used on most oral/nasal masks, thus allowing for a low profile interface that keeps the patient's line of sight unobstructed. The T-Flap portion can be made of different materials or combination of materials. It can be selectively attachable to the support cushion. The T-Flap or any support overlapping on top of the sealing element provides direct support to strengthen the structure of the mask without limiting the sealing cushion's floatation ability to separate the support from the seal. The T-flap portion can have other shapes, such as "L" shaped or it can be rounded or it can have a combination of shapes.

Figure 16:
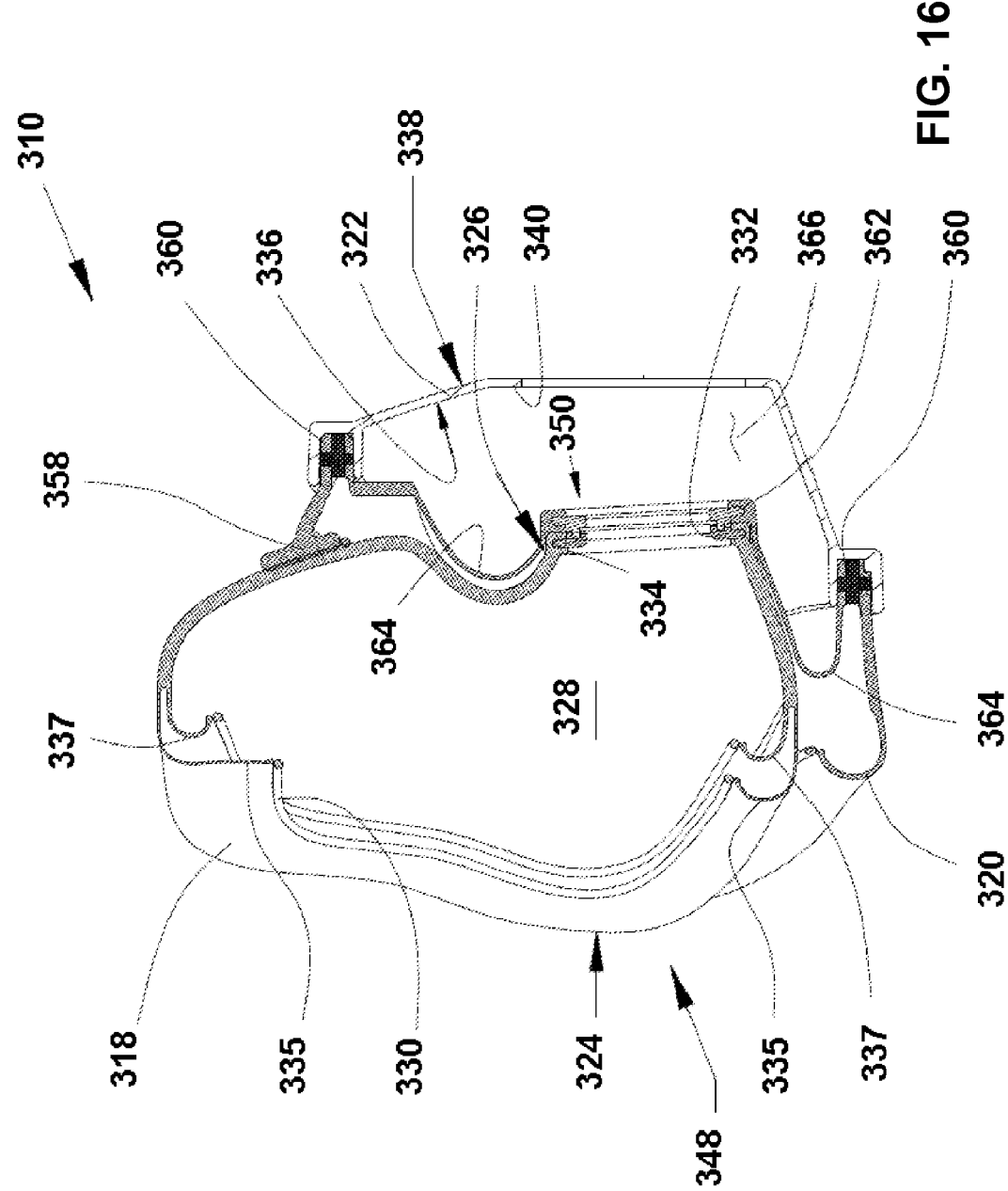
FIG. 16 is a cross-sectional view of the patient interface device of FIGS. 13-15 taken along line 16-16 of FIG. 15.
Figure 17:
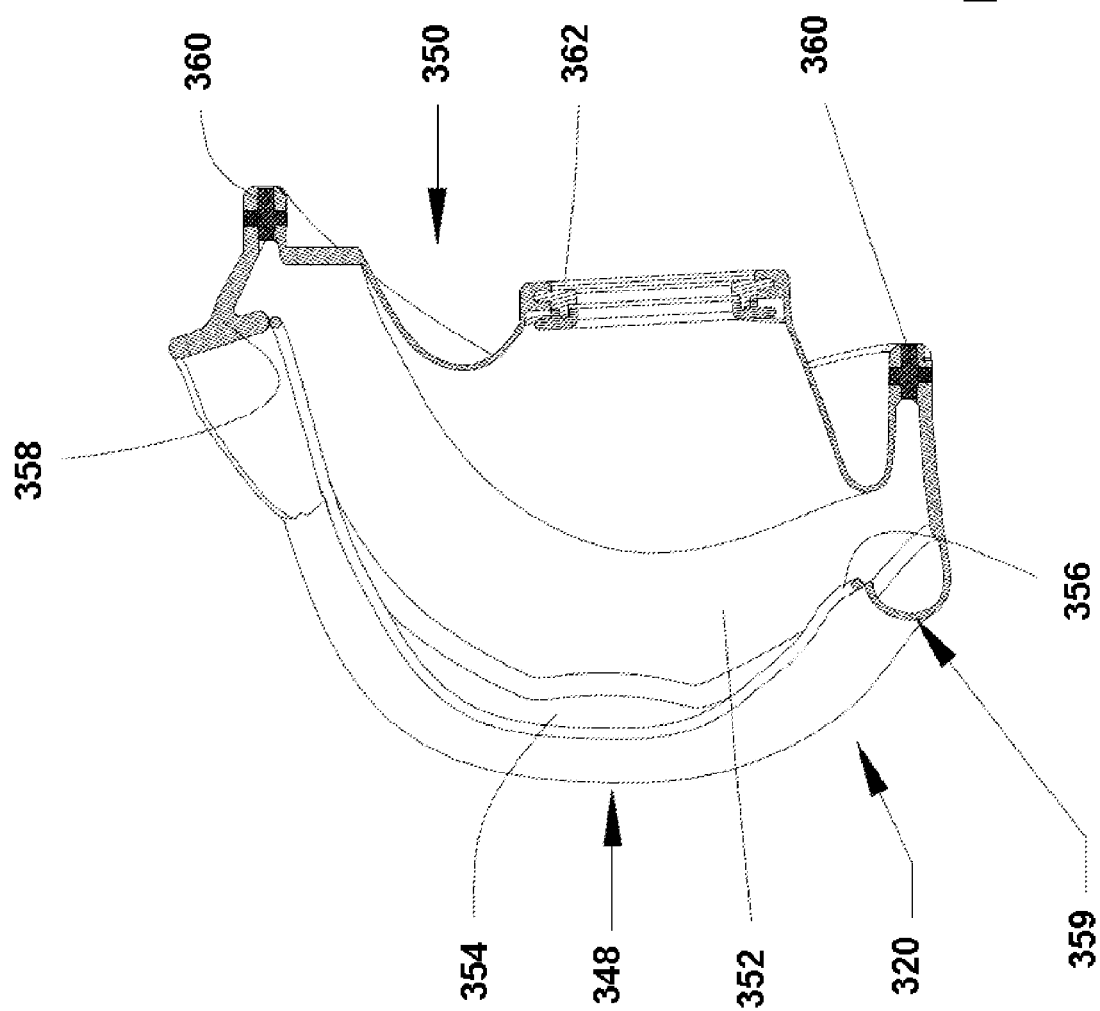
FIG. 17 is a cross-sectional view of a portion of the patient interface device of FIGS. 13-15 taken along line 16-16 of FIG. 15.
Figure 21:
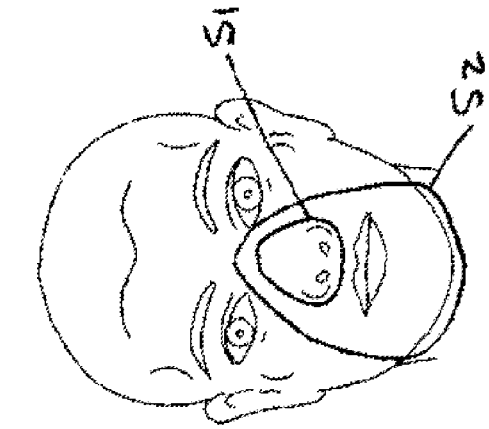
Figure 20:
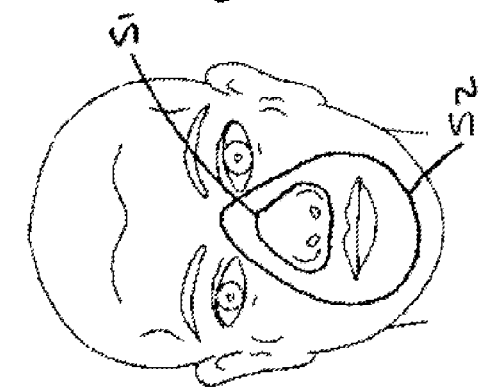
Figure 19:
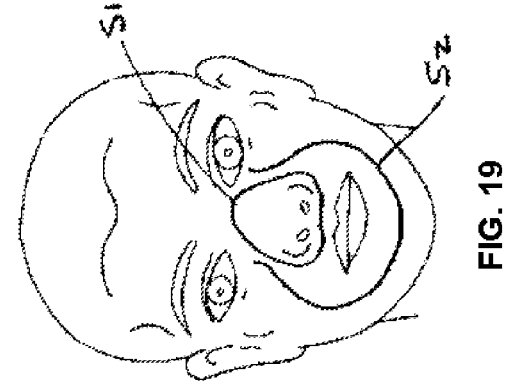
Figure 18:
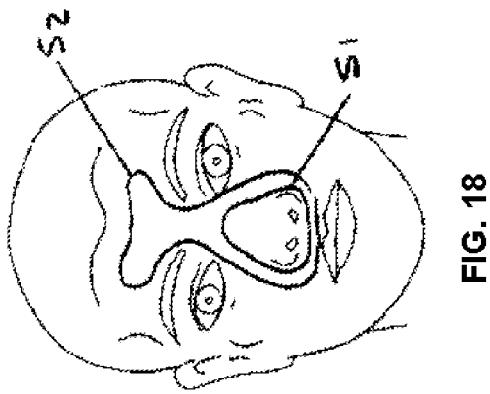
Figure 25:
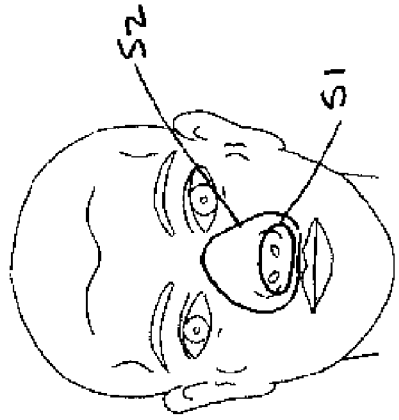
Figure 24:
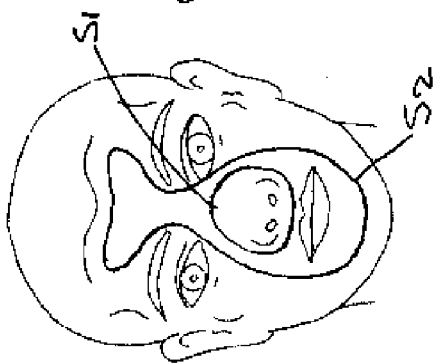
Figure 23:
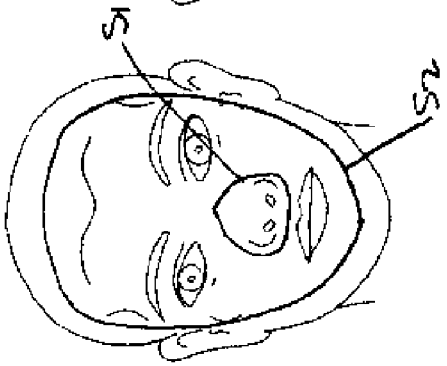
Figure 22:
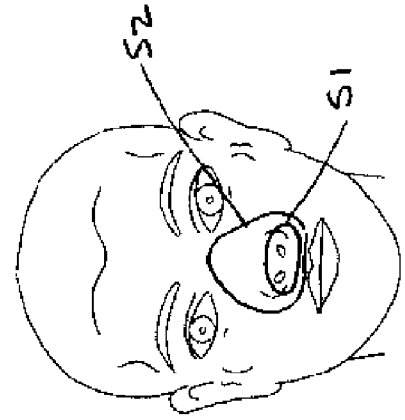
Figure 34:
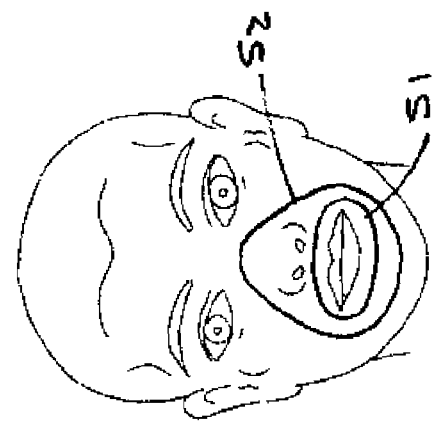
Figure 38:
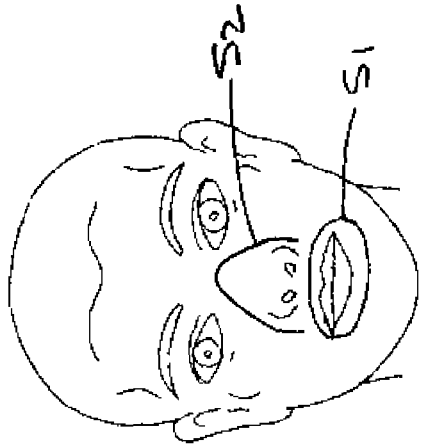
Figure 35:
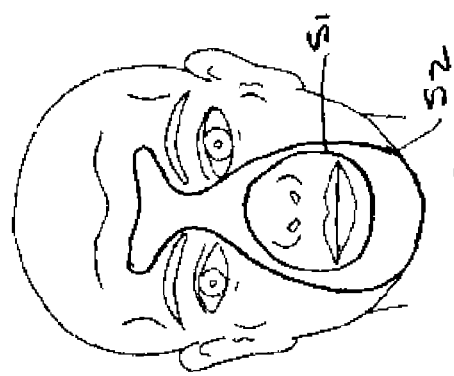
Figure 39:
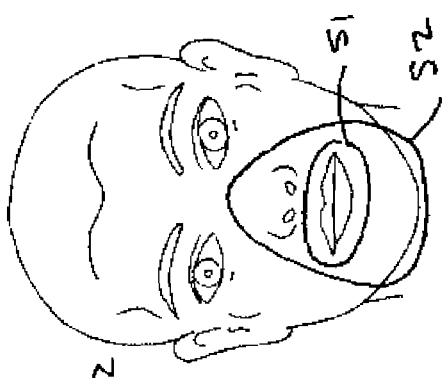
Figure 36:
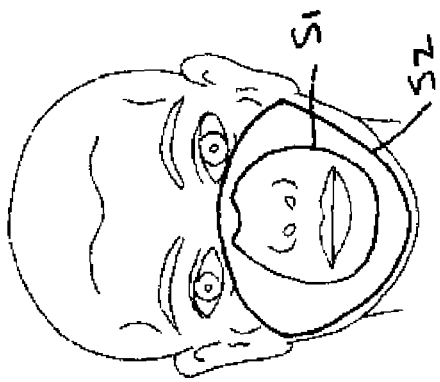
Figure 40:
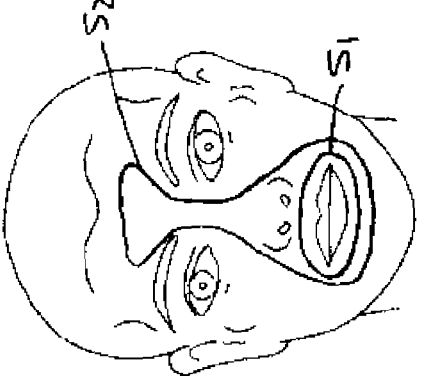
Figure 37:
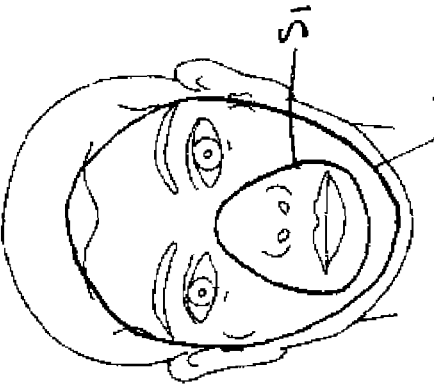
Figure 41:
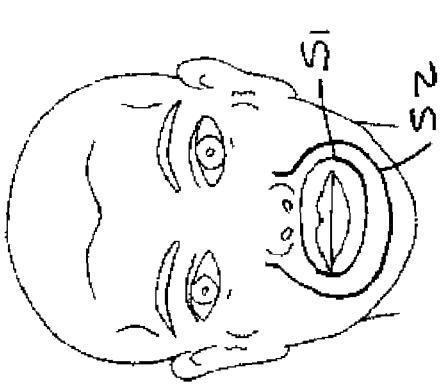
Figure 45:
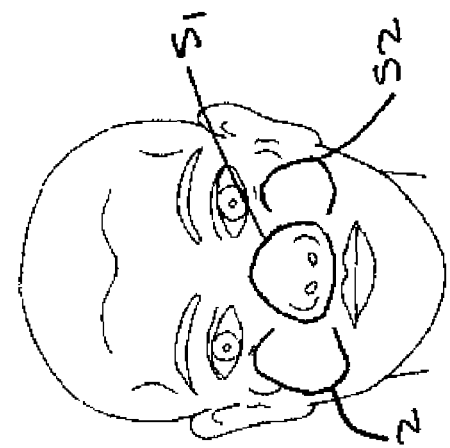
Figure 44:
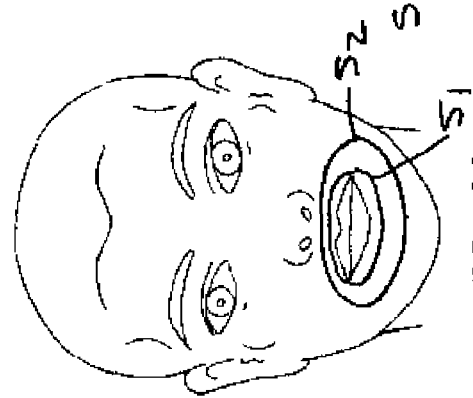
Figure 43:
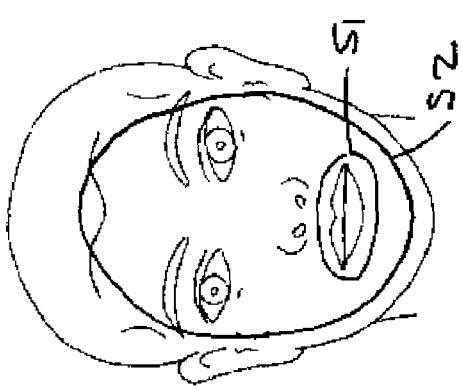
Figure 42:
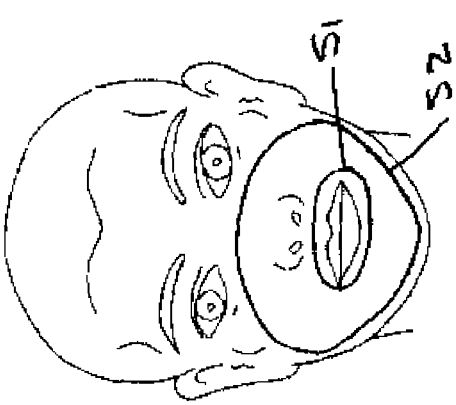
Figure 49:
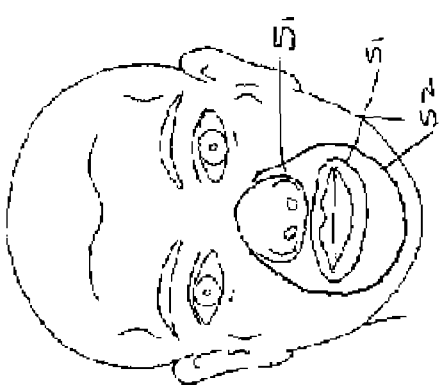
Figure 48:
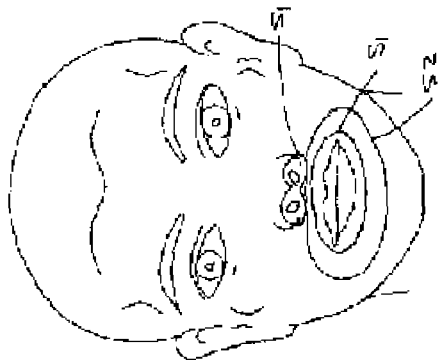
Figure 47:
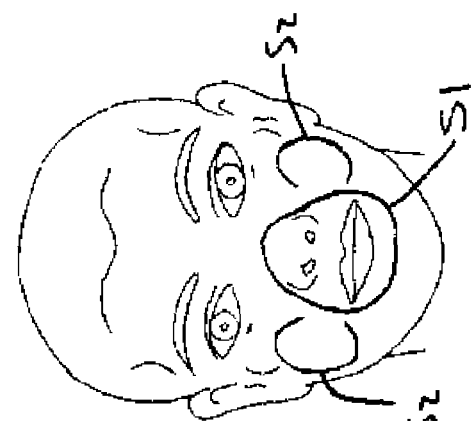
Figure 46:
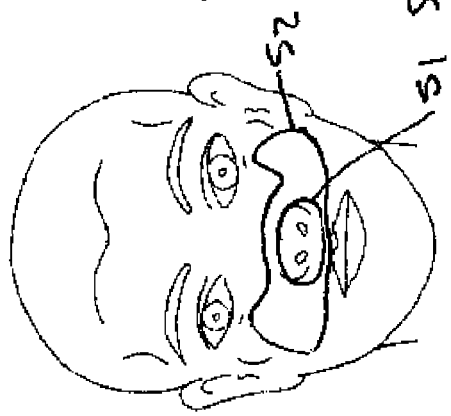
Figure 50:
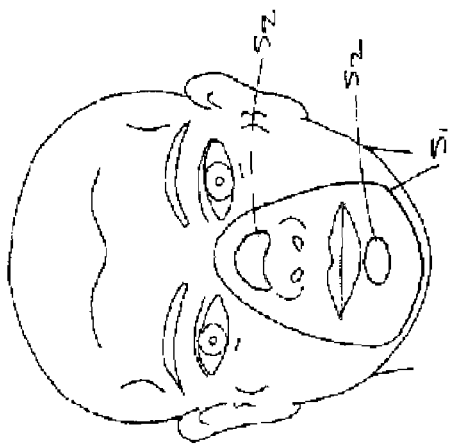

Second end portion 350 of support cushion 320 includes an outer portion 360, an inner portion 362, and a generally flexible portion 364 disposed therebetween. Outer portion 360 is configured to sealingly engage and be coupled to mask shell 322 as shown in FIG. 16. Continuing to refer to FIG. 16, inner portion 362 of second end portion 350 is configured to sealingly engage and be coupled to second end portion 326 of seal cushion 318 at or near base portion 332. As such, seal cushion 318 is coupled to mask shell 322 via generally flexible portion 364 of support cushion 320. Flexible portion 364 can change its shape depending on the force imparted to it through seal cushion 318 or mask shell 322 so that the position of the seal cushion relative to the mask shell can change.

Flexible portion 364 isolates the forces and acts as a buffer between seal cushion 318 and mask shell 322. Flexible portion 364 also acts as a flexible joint allowing relative angular and displacement movement between seal cushion 318 and mask shell 322. This allows seal cushion 318 to self-align on the surface of the patient when the patient interface device 310 is donned by the patient. Flexible portion 364 also isolates seal cushion 318 from movement of the patient's head or support cushion 320 and displacement of the conduit tubing 314 or headgear.

A mounting arrangement among seal cushion 318, support cushion 320, and mask shell 322 provides a reservoir 366 between second end portion 350 of support cushion 320 and patient side 336 of mask shell 322. Reservoir 366 effectively functions as a water trap for any water or other fluid that may enter the mask from conduit 314. Water or other fluid may condense on the walls of conduit 14, especially when a humidifier is used in the pressure/flow generating system. This fluid may flow toward the mask from pressure/flow generating device 312 and collect in reservoir 366. Thus, reservoir 366 effectively functions as a water trap to prevent or minimize the change of fluid contacting the user.

The present invention contemplates an alternative embodiment in which seal cushion 318 and support cushion 320 are formed as a single integral cushion, having an inner seal portion coupled to an outer support cushion similar to the embodiment described above.

Figure 60:
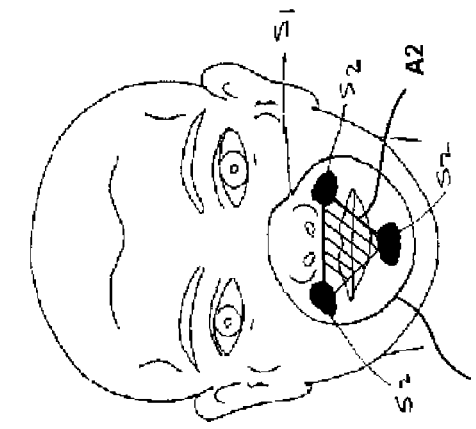
FIGS. 59 and 60 are schematic diagrams illustrating the first and second areas over a patient defined by the seal cushion and the support cushion, respectively.
Figure 59:
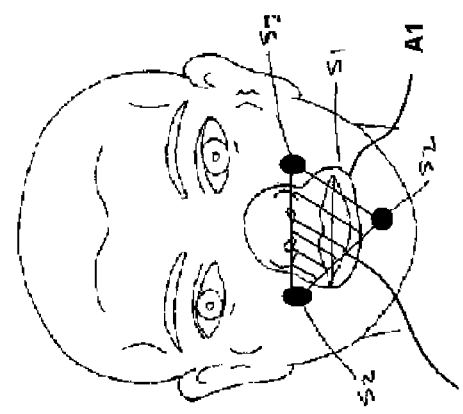

FIGS. 18-58 are schematic diagrams illustrating variously exemplary alternative embodiment for the engagement of the seal and support cushions on a face of a user. In these figures, the seal cushion is designed as "S1" and the support cushion is designated as "S2". More specifically, line S1 shows where on the face of the user the seal cushion is in contact with the user. The area bounded by line S1 corresponds to the first area noted above. In FIGS. 59 and 60, the first area is identified as A1.

Line S2 in FIGS. 18-58 shows where on the face of the user the support cushion is in contact with the user. The area bounded by line SS corresponds to the second area noted above. The present invention contemplates that the support cushion can contact the user over a second area that entirely overlaps or contains the first area (see, e.g., FIGS. 18, 20-29, 32, 34-40, 42-44, and 46). The present invention also contemplates that the second area defined by the support cushion does not entirely overlap or encompass the first area (see, e.g., FIGS. 19, 30, 31, 33, 41, 45, and 47, as well as the embodiments shown in FIGS. 13-18).

In some embodiments, the seal cushion S1 includes multiple seal cushions. For example, in FIGS. 48 and 49, one seal cushion is provided over the nose and another is provided over both nares. In the embodiment shown in FIG. 48 only the seal cushion over the mouth is overlapped by the second area defined by the support cushion S2.

Figure 51:
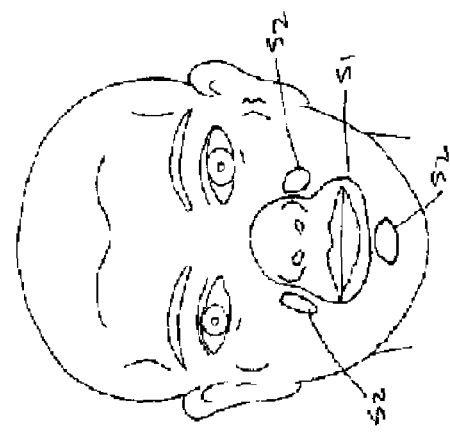

FIG. 51 illustrates an embodiment in which the support cushion includes multiple contact points around the perimeter of the seal cushion. Taken collectively, these multiple contact points define the second area that overlaps, at least partially, the first area defined by the perimeter of the seal cushion. FIGS. 59 and 60 are provided to show how the second area A2 is defined when the support cushion includes multiple contact points on the user. In FIGS. 59 and 60, second area A2 is defined by connecting each of the separate patient contacting points or area of the support cushion. When considered in this manner, second area A2 overlaps with at least a portion of first area A1.

Figure 52:
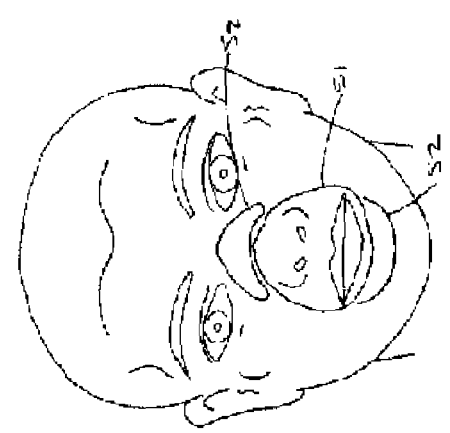
Figure 53:
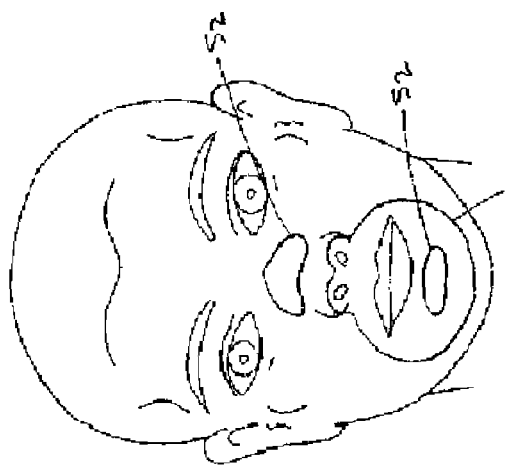
Figure 54:
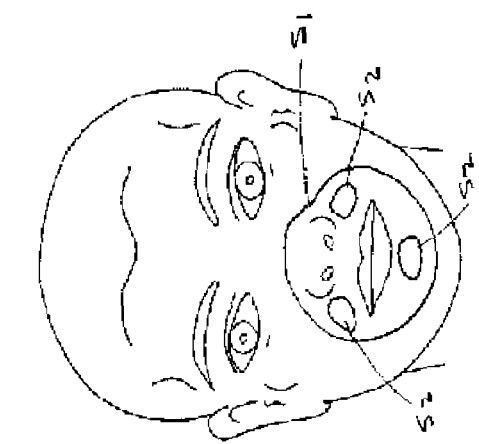

FIGS. 52 and 53 illustrate an embodiment in which the support cushion S2 is within the first area defined by the seal cushion S1. Even in this embodiment, the second area defined by either each support cushion or by the combination of the two support cushion shown, overlaps, at least partially, the first area defined by the seal cushion. Albeit in this embodiment the second area is entirely contained within the first area. In FIG. 54 the support cushion is defined by inside and outside the first area defined by the seal cushion.

Figure 57:
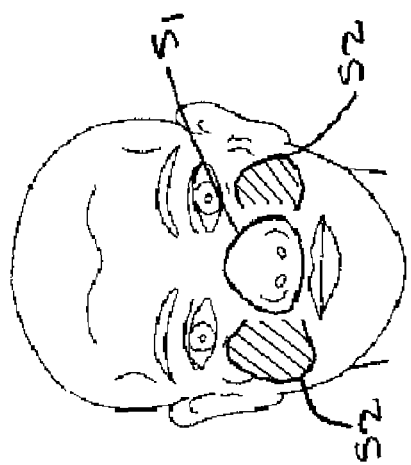
Figure 58:
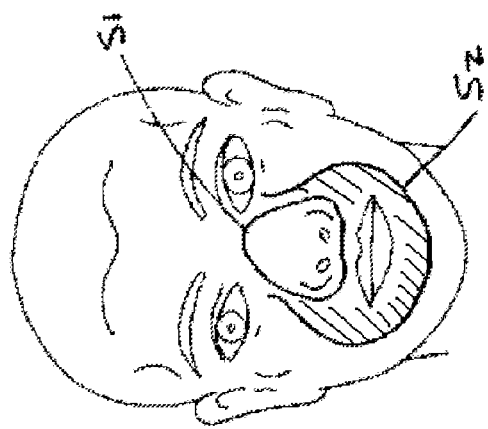

FIGS. 55-58 are generally similar to FIGS. 51, 53, 45 and 19, respectively, except that these figures show the support cushion S2 as contacting a larger area on the user than the earlier figures. In FIGS. 57 and 58, the contacting area of the support cushion is shaded. The present invention contemplates that the support cushion can have a relatively large contact area on the surface of the user, for example, to distribute the forces over a larger area, and need not be defined by a discrete sealing line.

Figure 56:
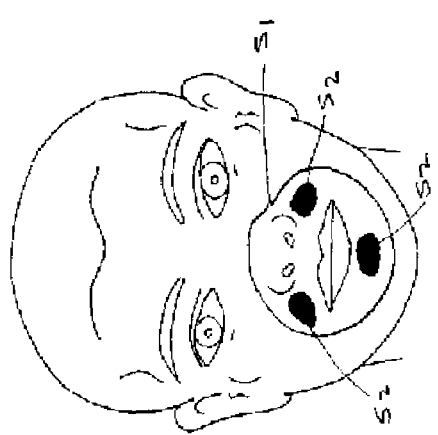
Figure 55:
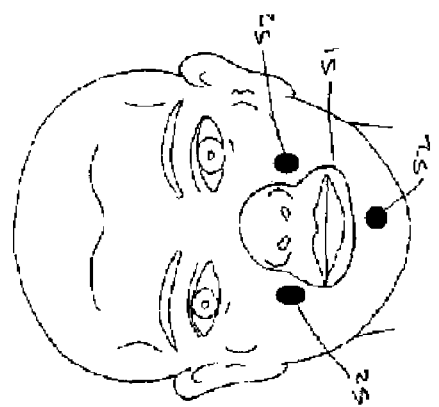

It should emphasized that the support cushion, as long as it is separate from the seal cushion, i.e., provided that they are not in a unitary embodiment, can be either completely and/or partially outside of the circumference of the seal cushion or the support cushion can be inside the circumference of the seal cushion. Separate support portion, i.e., both outside or inside the circumference of the seal cushion, can be substantially smaller than the sealing cushion as shown in FIGS. 55 and 56.

Moreover, it can be appreciated that the present invention contemplates that the support cushion does not get become compressed through the compression of the seal cushion, as this case, for example, in a double-flap cushion. The support cushion can contact the user, or become otherwise compressed, directly, independent of the position of the sealing cushion.

The patient interface device of any or all of the embodiments of the present invention communicates a flow of breathing gas between the patient's airway and pressure generating device 12, such as a ventilator, CPAP device, or variable pressure device, e.g., an auto-titrating pressure support device or a BiPAP® device manufactured and distributed by Respironics, Inc. of Pittsburgh, Pa., in which the pressure provided to the patient varies with the patient's respiratory cycle so that a higher pressure is delivered during inspiration than during expiration or an auto-titratition pressure support system where the pressure varies with the condition of the patient, such as whether the patient is snoring or experiencing an apnea or hypopnea.

Communicating a flow of breathing gas between the patient's airway and a pressure/flow generating device 12 includes delivering a flow of breathing gas to the patient from the pressure generating device 12 and exhausting a flow of gas from the patient to ambient atmosphere in the case of single-limb circuit. The system for delivering a pressurized flow of breathing gas to a patient according to the present invention comprises a pressure or gas flow generating device 12 that produces a flow of gas, a conduit 14 having a first end portion operatively coupled to the gas flow generating device 12 and a second end portion, wherein conduit 14 carries the flow of gas from gas flow generating device 12 during operation of the system; a patient interface device 10 coupled to the second end portion of the conduit; and a headgear. The interior of seal cushion 18 is exposed to the pressurized breathable gas. It is to be understood that other accessories used in a pressure support system, such as a humidifier, pressure sensor, flow sensor, temperature sensor, humidity sensor, bacteria filter, etc. can be used in conjunction with the patient interface device of the present invention.

It can also be appreciated that the description of the present invention, while discussing some different embodiments for the seal and mask, is not intended to be an exhaustive listing of the seals and masks suitable for use with the patient interface device of the present invention. On the contrary, those skilled in the art can appreciate that the mask shell, the seal cushion, the support cushion, and the components used to connect these elements to one another can have almost any configuration or size and still be used in conjunction with the patient interface device of the present invention.

It should be understood that the present invention contemplates that the seal cushion and the support cushion can have a variety of configurations, including those of conventional cushions. For example, the present invention contemplates forming either of these cushions from a gel material, as disclosed, for example, in U.S. Pat. Nos. 5,647,357 and 5,884,624, the contents of which are incorporated herein by reference, or from a gel material that is customizable, as disclosed, for example, in U.S. Pat. No. 6,397,847, the contents of which are incorporated herein by reference. The present invention also contemplates that the seal cushion, the support cushion, or both can be an air-filled cushion and can include an optional sealing flap. See, e.g., U.S. Pat. No. 4,791,051. These cushions can include features typically found in conventional cushion, such as stiffening devices, materials, and/or geometries and can be formed from any one of a variety of materials, such as silicone, or a combination of materials.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for use in delivering a flow of gas to an airway of a patient, the patient interface device comprising:
   (a) a mask shell having a patient side and an outer side opposite the patient side adapted to receive a flow of gas; and
   (b) a cushion assembly comprising:
      (1) a seal cushion having a first end portion structured to contact a patient's face to form a seal therewith and a second end portion opposite the first end portion, the seal cushion further including a cavity structured to receive a portion of the patient's face, wherein the flow of gas communicates with the cavity, wherein the seal cushion seals around an airway of such a patient, and wherein the seal cushion defines a first area over a face of such a patient responsive to the patient interface device being worn by such a patient, and
      (2) a support cushion having a first end portion adapted to contact a surface of a patient and a second end portion, wherein the support cushion defines a second area over such a patient responsive to the patient interface device being worn by such a patient, and wherein the second area overlaps at least a portion of the first area responsive to the patient interface device being worn by such a patient.

2. The patient interface device of claim 1, wherein the first end portion of the support cushion includes a lower portion structured to contact a patient's face, and an upper portion adapted to engage an upper portion of the seal cushion in the nose bridge area of such a patient, and wherein the second end portion of the seal cushion and the second end portion of the support cushion are coupled to the patient side of the mask shell.

3. The patient interface device of claim 1, wherein the seal cushion is configured so as to seal around a patient's nares, a mouth, or both a mouth and nares of such a patient.

4. The patient interface device of claim 1, wherein the upper portion of the first end portion of the support cushion comprises a more rigid structure than a remaining portion of the first end portion of the support cushion.

5. The patient interface device of claim 4, wherein the more rigid structure comprises a generally T-shaped cross-section, L-shaped cross-section, or rounded cross-section.

6. The patient interface device of claim 1, wherein the support cushion comprises a generally flexible member at or near the second end portion, and wherein the second end portion of the seal cushion is coupled to the generally flexible member such that the seal cushion is coupled to the mask shell via the generally flexible member.

7. The patient interface device of claim 1, wherein the cushion assembly comprises a unitary member and wherein the seal cushion comprises a first portion of the unitary member and wherein the support cushion comprises a second portion of the unitary member.

8. The patient interface device of claim 1, wherein one of the first end portion of the seal cushion, the first end portion of the support cushion, or both include at least one flap, two flaps at least partially overlying one another, a gas filled cushion, a gel material, or a combination thereof.

9. The patient interface device of claim 1, wherein the first end portion of the seal cushion, the first end portion of the support cushion, or both are contoured.

10. The patient interface device of claim 1, wherein the second area completely encompasses the first area responsive to the patient interface device being worn by such a patient.

11. The patient interface device of claim 1, wherein the second area is disposed with the first area responsive to the patient interface device being worn by such a patient.

12. The patient interface device of claim 1, wherein the support cushion comprises a first support cushion, and a second support cushion, and wherein the first and the second support cushions together define the second area.

13. The patient interface device of claim 1, wherein the seal cushion, the support cushion, or both include a grooved area defined in a portion thereof.

* * * * *